(12) United States Patent
Patten et al.

(10) Patent No.: US 6,365,377 B1
(45) Date of Patent: Apr. 2, 2002

(54) RECOMBINATION OF INSERTION MODIFIED NUCLEIC ACIDS

(75) Inventors: Phillip A. Patten; Volker Heinrichs, both of Mountain View; Willem P. C. Stemmer, Los Gatos, all of CA (US)

(73) Assignee: Maxygen, Inc., Redwood City, CA (US)

(*) Notice: Subject to any disclaimer, the term of this patent is extended or adjusted under 35 U.S.C. 154(b) by 0 days.

(21) Appl. No.: 09/517,933

(22) Filed: Mar. 3, 2000

Related U.S. Application Data

(60) Provisional application No. 60/122,943, filed on Mar. 5, 1999, provisional application No. 60/142,299, filed on Jul. 2, 1999, provisional application No. 60/164,617, filed on Nov. 10, 1999, and provisional application No. 60/164,618, filed on Nov. 10, 1999.

(51) Int. Cl.[7] .......................... C12P 19/34; C12Q 1/68; C12N 15/63; C12N 15/87; G01N 33/00
(52) U.S. Cl. .................... 435/91.1; 435/6; 435/455; 435/463; 436/94
(58) Field of Search .................... 435/6, 91.1, 91.2, 435/183, 91.51, 463, 455, 69.1; 436/94; 536/23.1, 24.3, 24.33, 25.3

(56) References Cited

U.S. PATENT DOCUMENTS

| | | |
|---|---|---|
| 5,252,745 A | 10/1993 | Reth |
| 5,264,563 A | 11/1993 | Huse |
| 5,470,725 A | 11/1995 | Borriss et al. |
| 5,496,714 A | 3/1996 | Comb |
| 5,498,531 A | 3/1996 | Jarrell |
| 5,512,463 A | 4/1996 | Stemmer |
| 5,514,588 A | 5/1996 | Varadaraj |
| 5,523,388 A | 6/1996 | Huse |
| 5,603,793 A | 2/1997 | Stemmer |
| 5,605,793 A | * 2/1997 | Stemmer .................... 435/6 |

(List continued on next page.)

FOREIGN PATENT DOCUMENTS

| | | |
|---|---|---|
| EP | 0229046 B1 | 5/1994 |
| EP | 0602899 A2 | 6/1994 |
| EP | 0544809 B1 | 12/1998 |
| EP | 0563296 B1 | 3/1999 |
| EP | 0911396 A2 | 4/1999 |
| EP | 0911396 A3 | 5/1999 |
| EP | 0934999 A1 | 8/1999 |
| WO | WO 86/05513 | 9/1986 |
| WO | WO86/05803 | 10/1986 |
| WO | WO90/14424 | 11/1990 |

(List continued on next page.)

OTHER PUBLICATIONS

Holford, et al., "Adding 'spice' to protein engineering," *Structure*, Aug. 15, 1998, 6:951–956.

Affholter & Arnold Engineering a revolution. *Chemistry in Britain* 35:48–51.

Affholter & Arnold, Engineering a revolution. *Chemtech* 29:34–39.

Affholter and Stemmer (1998) Directed evolution of proteins and pathways by DNA shuffling Book of Abstracts, 216th ACS National Meeting Boston, Aug. 23–27, BTEC–042.

Carlo (1996) "An intron splicing enhancer containing a G–rich repeat facilitates inclusion of a vertebrate micro–exon." *RNA* 2:342–353.

(List continued on next page.)

*Primary Examiner*—Ethan Whisenant
*Assistant Examiner*—Frank Lu
(74) *Attorney, Agent, or Firm*—Norman J. Kruse; Jonathan Alan Quine; Law Offices of Jonathan Alan Quine

(57) ABSTRACT

Methods of modulating, tuning and improving hybridization properties and recombination properties of molecules for use in nucleic acid shuffling procedures, relates recombination mixtures and methods of modulating, tuning, improving and evolving splicing of RNAs and proteins are provided.

35 Claims, 5 Drawing Sheets

U.S. PATENT DOCUMENTS

| | | |
|---|---|---|
| 5,667,969 A | 9/1997 | Sullenger |
| 5,698,426 A | 12/1997 | Huse |
| 5,723,323 A | 3/1998 | Kauffman et al. |
| 5,763,192 A | 6/1998 | Kauffman et al. |
| 5,763,239 A | 6/1998 | Short et al. |
| 5,770,434 A | 6/1998 | Huse |
| 5,776,744 A | 7/1998 | Glazer et al. |
| 5,780,272 A | 7/1998 | Jarrell |
| 5,789,228 A | 8/1998 | Lam et al. |
| 5,795,731 A | 8/1998 | Belfort |
| 5,808,022 A | 9/1998 | Huse |
| 5,811,238 A * | 9/1998 | Stemmer et al. ............... 435/6 |
| 5,814,473 A | 9/1998 | Warren et al. |
| 5,814,476 A | 9/1998 | Kaiffman et al. |
| 5,817,483 A | 10/1998 | Kauffman et al. |
| 5,824,469 A | 10/1998 | Horwitz et al. |
| 5,824,485 A | 10/1998 | Thompson et al. |
| 5,824,514 A | 10/1998 | Kauffman et al. |
| 5,830,696 A | 11/1998 | Short |
| 5,830,721 A | 11/1998 | Stemmer et al. |
| 5,834,247 A * | 11/1998 | Comb et al. ............... 435/69.7 |
| 5,834,252 A | 11/1998 | Stemmer et al. |
| 5,837,458 A | 11/1998 | Minushull et al. |
| 5,862,514 A | 1/1999 | Huse |
| 5,866,363 A | 2/1999 | Pieczenik |
| 5,869,254 A | 2/1999 | Sullenger |
| 5,871,974 A | 2/1999 | Huse |
| 5,872,241 A | 2/1999 | Pyle |
| 5,874,414 A | 2/1999 | Haseloff |
| 5,876,997 A | 3/1999 | Kretz |
| 5,891,993 A | 4/1999 | Dawson et al. |
| 5,910,437 A | 6/1999 | Kent et al. |
| 5,916,810 A | 6/1999 | Jarvik |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,955,358 A | 9/1999 | Huse |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,976,862 A | 11/1999 | Kauffman et al. |
| 5,981,182 A | 11/1999 | Jacobs |
| 5,985,646 A | 11/1999 | Murphy et al. |
| 6,001,574 A | 12/1999 | Short et al. |
| 6,004,788 A | 12/1999 | Short |
| 6,010,884 A | 1/2000 | Griffiths |
| 6,013,487 A | 1/2000 | Mitchell |
| 6,030,779 A | 2/2000 | Short |
| 6,054,267 A | 4/2000 | Short |
| 6,057,103 A | 5/2000 | Short |
| 6,087,341 A | 7/2000 | Khavari et al. |
| 6,096,548 A | 8/2000 | Stemmer |
| 6,117,679 A | 9/2000 | Stemmer |
| 6,132,970 A | 10/2000 | Stemmer |

FOREIGN PATENT DOCUMENTS

| | | |
|---|---|---|
| WO | WO90/14443 | 11/1990 |
| WO | WO92/03461 | 3/1992 |
| WO | WO92/06176 | 4/1992 |
| WO | WO92/06204 | 4/1992 |
| WO | WO92/11272 | 7/1992 |
| WO | WO 92/13090 | 8/1992 |
| WO | WO94/11496 | 5/1994 |
| WO | WO 94/16092 | 7/1994 |
| WO | WO 95/07351 | 3/1995 |
| WO | WO 95/15388 | 6/1995 |
| WO | WO 95/22625 | 8/1995 |
| WO | WO 96/33207 | 10/1996 |
| WO | WO 97/01642 | 1/1997 |
| WO | WO 97/07205 | 2/1997 |
| WO | WO 97/20078 | 6/1997 |
| WO | WO 97/25410 | 7/1997 |
| WO | WO 97/33957 | 9/1997 |
| WO | WO 97/35957 | 10/1997 |
| WO | WO 97/35966 | 10/1997 |
| WO | WO 96/34878 | 11/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/28434 | 7/1998 |
| WO | WO98/31816 | 7/1998 |
| WO | WO 98/31837 | 7/1998 |
| WO | WO 98/36080 | 8/1998 |
| WO | WO 98/40394 | 9/1998 |
| WO | WO 98/40519 | 9/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/49274 | 11/1998 |
| WO | WO 98/49275 | 11/1998 |
| WO | WO 98/58085 | 12/1998 |
| WO | WO99/06834 | 2/1999 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/11655 | 3/1999 |
| WO | WO99/19506 | 4/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO99/29902 | 6/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO99/51774 | 10/1999 |
| WO | WO 99/57128 | 11/1999 |
| WO | WO 99/65927 | 12/1999 |
| WO | WO00/04190 | 1/2000 |
| WO | WO00/06718 | 2/2000 |
| WO | WO00/09682 | 2/2000 |
| WO | WO00/09727 | 2/2000 |
| WO | WO00/12680 | 3/2000 |
| WO | WO 00/17342 | 3/2000 |
| WO | WO00/18778 | 4/2000 |
| WO | WO 00/18881 | 4/2000 |
| WO | WO00/18906 | 4/2000 |
| WO | WO00/20573 | 4/2000 |
| WO | WO00/28008 | 5/2000 |
| WO | WO00/28017 | 5/2000 |
| WO | WO00/28018 | 5/2000 |

OTHER PUBLICATIONS

Crameri et al., (1993) $10_{20}$—Fold aptamer library amplification without gel purification *Nuc. Acid Res.* 21(18):4410.

Howard, (1998) Chemistry of the future: Exploitation of the power of biology. Book of Abstracts, 216th ACS National Meeting Boston, Aug. 23–27, BTEC–045.

Leong et al., Maximizing the genetic diversity by molecular breeding: evolution of DNA vaccine vectors and adjuvant cytokines. 1999 Winter Biotechnology Conference: Molecular Approaches to Vaccine Design. Dec. 2–5 (1999).

Merz A., et al., Improving the catalytic activity of a thermophilic enzyme at low temperatures. *Biochemistry* 39(5) 880–889.

Minshull and Stemmer (1999) Protein evolution by molecular breeding *Current Opinion in Chem. Biol.* 3:284–290.

Patten et al., (1997) Applications of DNA shuffling to pharmaceuticals and vaccines. *Current Opinion in Biotech.* 8:724–733.

Punnonen et al., (1998) Evolution of genetic vaccines by DNA shuffling *Keystone Symposium on Molecular Aspect of Viral Immunity Tamarron*, CO, Feb. 16–22, 1998.

Punnonen et al., Evolution of DNA vaccine vectors, antigens, and adjuvant cytokines by DNA shuffling *Keystone Symposium on DNA vaccines*, Snowbird, UT, Apr. 12–17, 1999.

Punnonen J., Molecular breeding of allergy vaccines and antiallergic cytokines. *International Archives of Allergy and Immunology* 121:173–182.

Punnonen, et al., (1997) Evolution of DNA vaccine vectors by DNA shuffling The First Gordon Conference on Genetic Vaccines/DNA Vaccines Plymouth State College, Plymouth, NH, Jul. 20–25, 1997.

Soong et al., (1998) Directed evolution of novel retroviral tropisms by DNA shuffling Abstract #97, Programs & Abstracts, 1st Annual Meeting of the American Society of Gene Therapy May 28–31, 1998, Seattle, WA.

Soong et al., "Directed evolution of novel retroviral tropisms by DNA shuffling" Abstract, Retroviruses, 1998 Meeting, May 26–31, 1998 Cold Spring Harbor Laboratory, Cold Spring Harbor, NY.

Soong et al., "DNA shuffling as a tool to evolve desired retroviral phenotypes" Abstract, p. 228 *Gene Therapy, 1998 Meeting* Sep. 23–27, 1998 Cold Spring Harbor Laboratory, Cold Spring Harbor, NY.

Stemmer "Directed evolution of enzymes and pathways by DNA shuffling" FASEB Journal 13(7):A1431.

Stemmer et al., (1999) "Molecular Breeding of viruses for targeting and other clinical properties" *Tumor Targeting* 4:1–4.

Stemmer et al., Molecular evolution of genes and pathways by DNA shuffling. *FASEB Journal* 11(9):A1124.

Stemmer, Directed evolution of enzymes and pathways by DNA shuffling. Book of Abstracts, 217th ACS National Meeting, Anaheim, CA Mar. 21–25, BIOT–080.

Stemmer, Directed evolution of proteins, pathways, episomes and viruses by DNA shuffling *FASEB Journal* 12(8):A1303.

Stemmer, DNA sequence evolution by sexual PCR. Experientia (Basel) 52(ABSTR): A25.

Tobin et al., Colorless green ideas... *Nature Biotechnology* 17:333–334.

Welch et al., DNA shuffling of diverse natural genes to produce industrial enzymes with novel properties. Abstracts of the General Meeting of the American Society for Microbiology 99:507–508 Meeting info: 99th *General Meeting of the American Society for Microbiology*, Chicago, IL May 30–Jun. 3, 1999.

Wright et al., Evolution of viruses and vectors by DNA shuffling: Applications in vaccination and gene therapy. 1999 Winter Biotechnology Conference: Molecular Approaches to Vaccine Design. Dec. 2–5 (1999).

Crameri et al., (1993) "10(20)–Fold aptamer library amplification without gel purification," *Nuc. Acids Res.* 21(18):4410.

Patten, P.A. et al., (1997) "Application of DNA Shuffling to Pharmaceuticals and Vaccines." *Current Opinion in Biotechnology* 8:724–733.

Chang et al., (1999) "Evolution of a cytokine using DNA family shuffling" *Nature Biotechnology* 17:793–797.

Christians et al., (1999) "Directed evolution of thymidine kinase for AZT phosphorylation using DNA family shuffling" *Nature Biotechnology* 17:259–264.

Colston and Davis (1994) *Mol. Micobiol.*, 12:359–363.

Cook et al., "Photochemically initiated protein splicing" (1995) *Angew. Chem. Int. Ed. Engel 34*, 1620–1630.

Crameri and Stemmer (1995) "Combinatorial multiple cassette mutagenesis creates all the permutations of mutant and wildtype cassettes" *Bio Techniques* 18:194–195.

Crameri et al., (1996) "Construction and evolution of antibody–phage libraries by DNA shuffling" *Nature Medicine* 2:100–103.

Crameri et al., (1996) "Improved green fluorescent protein by molecular evolution using DNA shuffling" *Nature Biotechnology* 14:315–319.

Crameri et al., (1997) "Molecular evolution of an arsenate detoxification pathway by DNA shuffling" *Nature Biotechnology* 15:436–438.

Crameri et al., (1998) "DNA shuffling of a family of genes from diverse species accelerates directed evolution" *Nature* 391:288–291.

Davis et al., (1992) "Novel structure of the recA Locus of Mycobacterium . . . " *J. Bacteriol*, 173:5653–5662.

Davis et al., "Protein splicing in the maturation of M. Tuberculosis RecA Protein: A mechanism . . . " (1992) *Cell* 71:201–210.

Gates et al., (1996) "Affinity selective isolation of ligands from peptide libraries through display on a lac repressor headpiece dimer" *Journal of Molecular Biology* 255:373–386.

Hirtata et al., (1990) *J. Biol Chem.* 265:6726–6733.

Hodges et al., "Protein splicing removes intervening sequences in an archaea DNA polymerase" (1992) *Nucleic Acids Res.* 20:6153–6157.

Kane et al., (1990) "Protein splicing converts the yeast TFP1 Gene Product to the 69–kD Subunit . . . " *Science* 250:651–657.

Modefferi and Black (1997) *Mol Cell Biol.* 17:6537–6545.

Ness et al., (1999) DNA shuffling of subgenomic sequences of subtillsin *Nature Biotechnology* 17:893–896.

Ostermeier et al., "A combinatorial approach to hybrid enzymes independent of DNA homology" *Nature Biology* (1999) vol. 17 Dec. 1205–1208.

Perler et al., (1994) *Nucleic Acid Research* 22:1125–1127.

Stemmer (1994) "DNA shuffling by random fragmentation and reassembly: In vitro recombination for molecular evolution" *Proceedings of the National Academy of Sciences, USA* 91:10747–10751.

Stemmer (1994) "Rapid evolution of a protein in vitro by DNA shuffling" *Nature* 370:389–391.

Stemmer (1995) "Searching Sequence Space" *Bio/Technology* 13:549–553.

Stemmer (1995) "The Evolution of Molecular Computation" *Science* 270:1215.

Stemmer (1996) "Sexual PCR and Assembly PCR" *The Encyclopedia of Molecular Bioogy* pp 447–457.

Stemmer et al., (1995) "Single-step assembly of a gene and entire plasmid form large numbers of oligodeoxyribonucleotides" *Gene* 164:49–53.

Xu et al., (1993) *Cell* 75:1371–1377.

Zhang et al., (1997) "Directed evolution of an effective fucosidase from a galactosidease by DNA shuffling and screening" *Proceedings of the National Academy of Sciences, U.S.A.* 94:4504–4509.

Carlo et al., An intron splicing enhancer containing a G-rich repeat facilitates inclusion of a vertebrate micro-exon. RNA, 2, 343–353, 1996.*

* cited by examiner

SEQUENCE LISTING

<160> NUMBER OF SEQ ID NOS: 1

<210> SEQ ID NO 1
<211> LENGTH: 190
<212> TYPE: DNA
<213> ORGANISM: 134 nt ISE found in chicken card. trop.

<400> SEQUENCE: 1

```
aaaatctctc ttcttctgcc ctccatgcct ggctgcagca aagggtaagt caggctgcat        60
gcctcccacc acacctgtgc tgcatgacac ctggggctga cctgcaacag aagtggggct       120
gagggaagga ctgtcctggg gactggtgtc agagcggggt tggtgactct caggatgccc       180
aaaatgccca                                                              190
```

RECOMBINATION OF INSERTION MODIFIED NUCLEIC ACIDS

CROSS-REFERENCES TO RELATED APPLICATIONS

This application is related to U.S. Ser. No. 60/122,943 "RECOMBINATION OF INSERTION MODIFIED NUCLEIC ACIDS" by Patten et al., filed Mar. 5, 1999, the disclosure of which is incorporated herein by reference. This application is also related to U.S. Ser. No. 60/142,299 "RECOMBINATION OF INSERTION MODIFIED NUCLEIC ACIDS" by Patten et al., filed Jul. 02, 1999, the disclosure of which is incorporated herein by reference. This application is also related to U.S. Ser. No. 60/164,617 "RECOMBINATION OF INSERTION MODIFIED NUCLEIC ACIDS" by Patten et al., filed Nov. 10, 1999, the disclosure of which is incorporated herein by reference. This case is also related to Patten et al. "ENCRYPTION OF TRAITS USING SPLIT GENE SEQUENCES AND ENGINEERED GENETIC ELEMENTS" U.S. Ser. No. 60/164, 618, Filed Nov. 10, 1999. The present application claims priority to and the benefit of each of these prior applications, pursuant to 35. U.S.C. 119(e).

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to molecular shuffling, and to splicing of nucleic acids and proteins.

BACKGROUND OF THE INVENTION

Nucleic acid shuffling provides for the rapid evolution of nucleic acids, in vitro and in vivo. Rapid evolution provides for the commercial production of encoded molecules (e.g., nucleic acids and proteins) with new and/or improved properties. Proteins and nucleic acids of industrial, agricultural and therapeutic value can be created or improved through shuffling procedures. A number of publications by the inventors and their co-workers describe nucleic acid shuffling and applications of this technology. For example, Stemmer et al. (1994) "Rapid Evolution of a Protein" *Nature* 370:389–391; Stemmer (1994) "DNA Shuffling by Random Fragmentation and Reassembly: in vitro Recombination for Molecular Evolution," *Proc. Natl. Acad. USA* 91:10747–10751; Stemmer U.S. Pat. No. 5,603,793 METHODS FOR IN VITRO RECOMBINATION; Stemmer et al. U.S. Pat. No. 5,830, 721 DNA MUTAGENESIS BY RANDOM FRAGMENTATION AND REASSEMBLY; Stemmer et al., U.S. Pat. No. 5,811,238 METHODS FOR GENERATING POLYNUCLEOTIDES HAVING DESIRED CHARACTERISTICS BY ITERATIVE SELECTION AND RECOMBINATION describe, e.g., in vivo and in vitro nucleic acid, DNA and protein shuffling in a variety of formats, e.g., by repeated cycles of mutagenesis, shuffling and selection, as well as methods of generating libraries of displayed peptides and antibodies.

Applications of DNA shuffling technology have also been developed by the inventors and their co-workers. In addition to the publications noted above, Minshull et al., U.S. Pat. No. 5,837,458 METHODS AND COMPOSITIONS FOR CELLULAR AND METABOLIC ENGINEERING provides for the evolution of metabolic pathways and the enhancement of bioprocessing through recursive shuffling techniques. Crameri et al. (1996), "Construction And Evolution Of Antibody-Phage Libraries By DNA Shuffling" *Nature Medicine* 2(1):100–103 describe, e.g., antibody shuffling for antibody phage libraries. Additional details regarding DNA Shuffling can also be found in WO95/22625, WO97/20078, WO96/33207, WO97/33957, WO98/27230, WO97/35966, W098/ 31837, WO98/13487, WO98/13485 and WO989/42832.

Physical nucleic acid shuffling techniques (as opposed, e.g., to "in silico" methods which are performed, at least in part, by manipulation of character strings in a computer) rely upon actual recombination between physical nucleic acids, whether the format is an in vitro or an in vivo format. Recombination occurs at a relatively high frequency, e.g., where there are complementary nucleic acids between strands to be recombined. Thus. nucleic acids to be recombined are typically e.g., about 70% identical/complementary in sequence over regions of, e.g., about 30–40 nucleotides. It would be desirable to be able to recombine low homology, or even non-homologous sequences, thereby increasing access to the potential sequence space encoded by recombinant nucleic acids resulting from shuffling methods. For example, for proteins which are commercially valuable, it would be desirable to be able to gain access to a recombination/mutation spectrum which is different than that of the native protein to provide for greater diversity in products produced by the various available shuffling strategies.

Similarly, nucleic acid recombination generally can be difficult to modulate, resulting in regions of high or low crossover frequency between two different targets for recombination. The crossover frequency for a particular pairing of sequences on two different targets is one feature that mediates the recombinant nucleic acids that result from recombination methods. Improved methods of modulating the recombination frequency at potential recombination sites would be desirable to weight/bias recombination product outcomes.

In general, new techniques which facilitate, improve or add levels of control to recombination methods are highly desirable. In particular, techniques which permit shuffling of divergent nucleic acids, or which provide for modulation and tuning of shuffling rates are desirable. The present invention provides such significant new recombination protocols, as well as other features which will be apparent upon complete review of this disclosure.

SUMMARY OF THE INVENTION

The present invention provides a number of new nucleic acid recombination formats for nucleic acid shuffling. In the methods, a number of insertion sequences are inserted into one or more parental nucleic acid to provide a modified target nucleic acid substrate for recombination and subsequent mutation. The number, type and placement of such insertion sequences provides for the ability to shuffle nucleic acids with little or no homology other than the insertion sequences. In addition, these insertion sequences provide for the ability to modulate or "tune" recombination frequencies between target nucleic acids. The methods typically take advantage of self-splicing, trans-splicing or use cellular machinery to remove the insertion sequences from final coded nucleic acids or proteins, e.g., where the insertion sequences are introns, inteins, proteolyzed polypeptide sequences or the like. The insertion sequences can also comprise markers, molecular tags, or the like, e.g., for purification of encoded molecules or can serve to allow for expression of otherwise toxic proteins (e.g., RNases, Dnases, restriction enzymes, proteases, lipases, recombinases, ligases, polymerases, etc.) e.g., in a form where an intein is excised in vivo. Similarly, in vitro expression of insertion modified sequences can result in the production of these and other proteins in vitro, e.g., using in vitro expression systems.

Methods of shuffling two target nucleic acids (i.e., a first and a second target nucleic acid) are provided. In the methods, a first and a second target nucleic acid are provided, e.g., by cloning, PCR amplification, synthesis, isolation from an environmental source (soil, air, water, etc.), or other methods. At least one of the first and second target nucleic acids (and typically both) have a plurality of homologous or non-homologous insertion nucleic acid sequences, such as one or more intron (e.g., self-splicing bacterial, eukaryotic or trans-splicing intron), intein, subsequence removed by site specific recombination (e.g., similar to V-D-J recombination for antibody production), or the like, optionally including intron splicing enhancers or the like. The target nucleic acids are recombined, producing a shuffled recombinant nucleic acid.

In addition to providing for new recombination methods per se, the invention also provides methods of producing selected proteins and RNAs, for any of the purposes that such proteins and RNAs are ordinarily produced. For example, in one aspect, a first shuffled nucleic acid subsequence encoding a first portion of the selected protein and a second nucleic acid subsequence encoding a second portion of the selected protein is provided. The nucleic adds can be on the same strand (as in cis-mediated reactions) or on different strands (as in trans mediated reactions). The first and second subsequences are expressed to produce a first protein subsequence and a second protein subsequence, which are spliced to produce the selected protein. Commonly, more than two subsequences are spliced, e.g., 3, 4, 5, 6, 7, 8, 9, 10 or more sequences, as set forth herein. The splicing reaction can be in cis or in trans (or both) and can be in viro or in vivo (or both). Splicing can occur by spontaneous or controlled mechanisms.

Similarly, in RNA production methods, a first shuffled nucleic acid subsequence encoding a first portion of the selected RNA is provided and a second nucleic acid subsequence encoding a second portion of the selected RNA is also provided. Again, these subsequences can be on the same or on different molecules (depending on whether cis or trans splicing is employed). The first and second nucleic acid subsequences, or RNA copies thereof, are spliced to produce the selected RNA, which can encode a useful RNA (e.g., an antisense, or sense molecule, or ribozyme) or the RNA can encode a protein. The intein and RNA shuffling/production methods are combinable, i.e., the spliced RNA molecules can encode intein-extein sequences which are spliced at the protein level to produce a useful protein.

In general, a parental nucleic acid can be broken into several exons or exteins by incorporation of a number of introns or inteins into the sequence of the parental nucleic acid. For example, the target nucleic acid resulting from incorporation of insertion sequences into the parental nucleic acid can have, e.g., about 5, 10, 15, 20, 30, 50, 100 or more "mini exons," or "mini exteins" separated by a corresponding number of insertion sequences.

In shuffling reactions, first and second target nucleic acids are optionally derived from a first and second parental nucleic acid which are sufficiently different in sequence that they do not substantially hybridize in solution. For example, the first and second target nucleic acids can be derived by integration of a plurality of insertion sequences into the first and second parental nucleic acid. The first and second parental nucleic acid can be, e.g., less than 50%, or less than e.g., 40%, or less than e.g., 30%, or less than e.g., 25% or less than e.g., 15% identical over the full length of the first and second parental nucleic acid, when the first and second nucleic acids are aligned for maximum identity.

The insertion nucleic acid sequences can modulate a recombination frequency between the first and second target nucleic acid. For example, by placing an intron into a parental sequence, the recombination efficiency of nucleic acid subsequences to either side of the intron can be decreased. Similarly, placing homologous mini introns within the parental sequences provides sites for recombination within the resulting targets, e.g., where the targets display regions of low similarity in non-intronic sequences.

Insertion sequences can also modulate expression in one or more cell type, e.g., where the insertion sequences comprise one or more enhancer or other regulatory sequence. Similarly, insertion sequences optionally comprise splicing enhancer sequences (e.g., ISEs, such as the chicken cardiac troponin T (cTNT) ISE) to facilitate splicing.

Essentially any nucleic acid can be a parental nucleic acid with which insertion sequences can be combined to produce a target nucleic acid for splicing. Example sequences include parental nucleic acids corresponding a gene or cDNA encoding EPO, a gene or cDNA encoding an insulin protein, a gene or cDNA encoding a peptide hormone, a gene or cDNA encoding a cytokine, a gene or cDNA encoding an epidermal growth factor, a gene or cDNA encoding a fibroblast growth factor, a gene or cDNA encoding a hepatocyte growth factor, a gene or cDNA encoding insulin-like growth factor, a gene or cDNA encoding an interferon, a gene or cDNA encoding an interleukin, a gene or cDNA encoding a keratinocyte growth factor, a gene or cDNA encoding a leukemia inhibitory factor, a gene or cDNA encoding oncostatin M, a gene or cDNA encoding PD-ECSF, a gene or cDNA encoding PDGF, a gene or cDNA encoding pleiotropin, a gene or cDNA encoding SCF, a gene or cDNA encoding c-kit ligand, a gene or cDNA encoding VEGF, a gene or cDNA encoding G-CSF, a gene or cDNA encoding an oncogene, a gene or cDNA encoding a tumor suppressor, a gene or cDNA encoding a steroid hormone receptor, a gene or cDNA encoding a plant hormone, a gene or cDNA encoding a disease resistance gene, a gene or cDNA encoding an herbicide resistance gene, a gene or cDNA encoding a bacterial gene, a gene or cDNA encoding a monooxygenase, a gene or cDNA encoding a protease, a gene or cDNA encoding a nuclease, an antibody, a peptide ligand, an angiogenisis inhibitor, a gene, or cDNA encoding a lipase, a gene or cDNA encoding a C-X-C chemokine, a gene or cDNA encoding a C—C chemokine, a gene or cDNA encoding an antibody V gene, a gene or cDNA encoding a cystein knot protein such as TGFβ, NGF, PDGFβ or the like, a gene or cDNA encoding a $TNK_{or}$ family member, a gene or cDNA encoding CNTF, a gene or cDNA encoding 4F, and/or gene or cDNA encoding an RNase.

The methods herein are amenable to both physical recombination of nucleic acids and to virtual or "in silico" recombination of character strings representing nucleic acids, e.g., in a computer. Following complete or partial sequence recombination in silico, target nucleic acids, or nucleic acids derived from the target nucleic acids can be synthesized. Such synthetic nucleic acids can be recombined, cloned, selected or otherwise manipulated in the same manner as any other nucleic acid.

A variety of techniques can be used to produce target nucleic acids comprising insertion sequences. Such methods include chemical synthesis, PCR concatemerization, in silico character string formation or generation, and the like. For example, in one embodiment, insertion of the plurality of insertion nucleic acid sequences into one or more of the first and second parental nucleic acid sequences is performed by physically joining a plurality of subsequences of the first or second parental nucleic acid sequences to the plurality of insertion nucleic acid sequences.

As noted, the addition of insertion sequences to parental nucleic acids can modify or modulate the recombination of resulting target nucleic acids. Similarly, the addition of insertion sequences can alter the hybridization properties of resulting target sequences. For example, even non-homologous parental nucleic acids can be made to hybridize by the addition of a sufficient number and appropriate arrangement of insertion sequences. Similarly, a target nucleic acid derived from a parental sequence can be made which does not hybridize under a selected set of conditions (e.g., stringent hybridization conditions) to the parental nucleic acid. As noted above, such insertion sequences can be used to tune recombination rates between selected regions of a target nucleic acid, e.g., where a particular region is targeted for an increased or decreased recombination rate.

The target and parental nucleic acids can have dramatically different hybridization properties as a result of the insertion sequences being present in the target nucleic acids. The target nucleic acids can be prevented from hybridizing to the parents by inclusion of the target sequences, or, conversely, one or more target sequence can even be made to hybridize to one or more parent, thereby controlling the recombination properties of resulting nucleic acid shuffling reactions. Thus, in one embodiment, the first and second parental nucleic acid sequences hybridize under stringent conditions, and the first and second target nucleic acids do not hybridize under stringent conditions. Similarly, in another embodiment, the first and second parental nucleic acid sequences do not hybridize under stringent conditions, while the first and second target nucleic acids hybridize under stringent conditions. In yet another embodiment, the first and second nucleic target nucleic acid hybridize under stringent conditions, while the first target nucleic acid does not hybridize under stringent conditions to the second parental nucleic acid, or wherein the second target nucleic acid does not hybridize under stringent conditions to the first parental nucleic acid. Similarly, in one embodiment, the first or second parental nucleic acid hybridizes to a third nucleic acid under stringent conditions, where the first and second target nucleic acids do not hybridize under stringent conditions to the third nucleic acid. A variety of other modifications in hybridization due to the number and arrangement of insertion sequences will be apparent upon complete review.

Recombinant nucleic acids generated by recombining nucleic acid sequences comprising insertion subsequences can, of course, be recombined or shuffled, cloned, amplified, expressed in vivo or in vitro, synthesized, or otherwise modified using any available naturally mediated or laboratory-mediated technique. For example, in one embodiment, a shuffled recombinant nucleic acid made by recombining one or more target nucleic acid comprising a plurality of insertion sequences with one or more additional nucleic acid(s) is recombined with a third nucleic acid. The resulting secondary shuffled recombinant nucleic acid can be selected for a desired trait or property using any available selection method. In general, any recombinant nucleic acid can be selected for a desired trait or property.

Recombinant nucleic acids are also optionally expressed in a cell or in vitro, thereby producing a nucleic acid or protein. In one embodiment, the expressed protein can comprise intein and extein sequences. Typically, the intein (some times referred to as an "intervening protein sequence") is excised from an expressed protein sequences. Concomitantly, the ligation of the flanking sequences (exteins) form a mature "extein protein" which is, optionally, active in one or more cell or in one or more in vitro reaction or system. Thus, expressed proteins can be proteolytically cleaved and ligated to produce an active protein, and/or to remove an intein from an expressed protein. This ligation reaction can occur both cis- and trans-splicing reaction formats. Reactions occur in vitro or in vivo for cis or trans splicing inteins. For additional details regarding trans splicing of introns and inteins. see, Patten et al. "ENCRYPTION OF TRAITS USING SPLIT GENE SEQUENCES AND ENGINEERED GENETIC ELEMENTS" U.S. Ser. No. 60/164,618 Filed Nov. 10, 1999.

The presence of insertion sequences can be used to modulate recombination rates between regions of nucleic acids. For example, the cross over frequency between two points on a first and second target nucleic acids can typically be increased by placing insertion sequences between the two points. This is desirable, e.g., where low linkage rates between regions of nucleic acids to be recombined are desired, e.g., where one wishes to separately evolve different functional domains or elements of the nucleic acid.

Recombinant nucleic acids can be modified by removal of insertion sequencres to improve expression or facilitate cloning of any final product. For example, where a nucleic acid encodes a plurality of intronic insertion sequences, the encoded mRNA can be reverse transcribed and the resulting cDNA cloned or otherwise manipulated. It should be noted that this process can result in a cDNA which does not hybridize to the recombinant nucleic acid comprising the introns. Indeed, the cDNA can be the result of several rounds of selection and recombination, resulting in a cDNA with a highly unique sequence which does not hybridize under e.g., stringent conditions, to any previously known sequence. Thus, sequence space which is inaccesible between two known nucleic acids is accessible by this procedure, resulting in recombinant products that could not otherwise be obtained.

The final product produced by any of the procedures herein can be a DNA (e.g., a genomic DNA, an artificial DNA, a cDNA, or the like), an RNA, an mRNA, a viral RNA, a sn RNA, a tRNA, an rRNA, a gRNA, a protein, a proteolytically cleaved protein, a protein fragment, a spliced protein or any other molcule that can be encoded by a nucleic acid, including e.g., metabolic products and the like. As noted, target sequences can comprise homologous or non homologous nucleic acid subsequences which can be separated by homologous or non homologous insertion sequences. The target nucleic acids to be recombined can be homologous relative to each other, or comprise homologous and non-homologous sequences relative to each other. The nucleic acids can be present in vectors such as expression vectors, or can be free in solution.

The nucleic acids to be recombined can be present in recombination mixtures. For example one recombination mixture of the invention includes a first target nucleic acid comprising a plurality of insertion subsequences. Typically, the mixture also includes a second target nucleic acid having at least one region of sequence similarity to the first nucleic acid. The second target nucleic acid typically also includes a plurality of insertion subsequences.

In one format, a recombination mixture resulting from fragmenting a first target nucleic acid comprising a plurality of insertion subsequences, and a second target nucleic acid comprising at least one region of sequence similarity to the first target nucleic acid is provided. For example, the first and second target nucleic acids can be fragmented with a DNase or, e.g., cleaved chemically to produce nucleic acid fragments. Similarly, the first and second target nucleic acids can be "fragmented" by chemically synthesizing fragments of the first and second target nucleic acid.

Recombinant nucleic acids produced by recombining the recombination mixtures of invention are also provided. For example, the first or second nucleic acid can include one or more subsequence corresponding to one or more subsequence from one or more gene or cDNA such as a gene or cDNA encoding EPO, a gene or cDNA encoding an insulin protein, a gene or cDNA encoding a peptide hormone, a gene or cDNA encoding a cytokine, a gene or cDNA encoding an epidermal growth factor, a gene or cDNA encoding a fibroblast growth factor, a gene or cDNA encoding a hepatocyte growth factor, a gene or cDNA encoding insulin-like growth factor, a gene or cDNA encoding an interferon, a gene or cDNA encoding an interleukin, a gene or cDNA encoding a keratinocyte growth factor, a gene or cDNA encoding a leukemia inhibitory factor, a gene or cDNA encoding oncostatin M, a gene or cDNA encoding PD-ECSF, a gene or cDNA encoding PDGF, a gene or cDNA encoding pleiotropin, a gene or cDNA encoding SCF, a gene or cDNA encoding c-kit ligand, a gene or cDNA encoding VEGF, a gene or cDNA encoding G-CSF, a gene or cDNA encoding an oncogene, a gene or cDNA encoding a tumor suppressor, a gene or cDNA encoding a steroid hormone receptor, a gene or cDNA encoding a plant hormone, a gene or cDNA encoding a disease resistance gene, a gene or cDNA encoding an herbicide resistance gene, a gene or cDNA encoding a bacterial gene, a gene or cDNA encoding a monooxygenase, a gene or cDNA encoding a protease, a gene or cDNA encoding a nuclease, a gene or cDNA encoding an RNase, and/or a gene or cDNA encoding a lipase. Of course, many other nucleic acids/proteins can be made or modified by the methods herein. The resulting recombinant nucleic acid can also comprise activities and subsequences which correspond to these nucleic acids.

In one aspect, the invention provides methods of recombining a plurality of sequence domains from a plurality of homologous or non-homologous nucleic acid sequences. In the methods, a pre-mRNA comprising a plurality of sequence domains is provided which correspond to a plurality of different parental nucleic acid sequences. The pre-mRNA is alternatively spliced to produce a plurality of different mRNAs comprising a plurality of different sets of sequence domains. Typically, the pre-mRNA has between about 6 and about 20 exons or exteins, e.g., where the pre-mRNA has a plurality of mini exons or exteins. Most typically, the plurality of different mRNAs are selected for a desired trait or property. Optionally, the methods include cloning one or more of the plurality of different mRNAs.

In this alternative splicing/recombination strategy, the methods typically include recombining one or more of: the plurality of different mRNAs, the pre-mRNA, a DNA encoding the mRNA, and a DNA encoding the pre-mRNA, with one or more additional nucleic acid.

In one embodiment, the pre-mRNA is provided to a cell by transducing or transfecting the cell with a vector comprising a DNA encoding the pre-mRNA. As discussed throughout, in vitro formats are also available.

The present invention also provides methods of making a nucleic acid with a desired splicing phenotype. In the methods, a plurality of homologous nucleic acids are provided, each comprising a plurality of insertion nucleic acid sequences. The plurality of homologous nucleic acids are recombined to produce a library of recombinant nucleic acids, which are selected for production of a desired or selected mRNA or protein (or product thereof) when the selected recombinant nucleic acid is expressed in vitro or in a cell. As with any nucleic acid noted above, this selected nucleic acid is optionally recombined with an additional nucleic acid and the resulting secondary recombinant nucleic acid selected for production of a desired mRNA or protein (or product thereof).

The nucleic acids noted above which include insertion sequences will typically comprise as many as 10 insertion sequences and as many as 10 flanking sequences (e.g., exons or exteins) or more. Insertion nucleic acid sequences include those derived from bacterial introns, eukaryotic introns and archaebacterial introns, as well as bacterial inteins, eukaryotic inteins and archaebacterial inteins. The nucleic acids are recombined in vitro or vivo.

The present invention also provides apparatus, integrated systems and kits for practicing the methods herein, e.g., comprising use of the recombination mixtures herein, containers, instruction sets for practicing the methods herein, and the like.

DEFINITIONS

Figure 1:
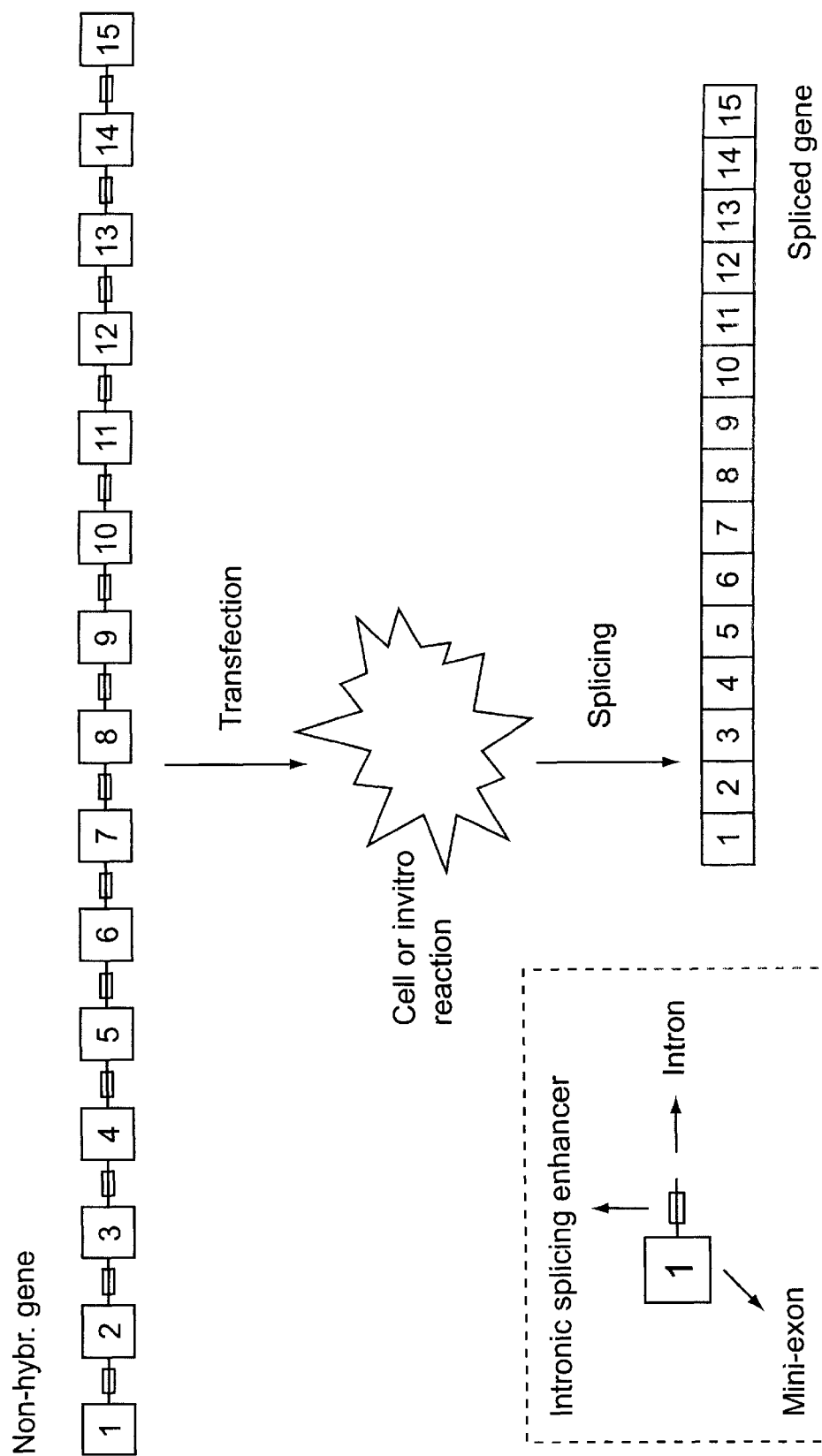
FIG. 1 is a schematic of a splicing procedure for creating non-hybridizing genes.

The following definitions supplement those in the art.

An "insertion nucleic acid subsequence" is a nucleic acid subsequence found in a full-length nucleic acid sequence, which subsequence is derived from a nucleic acid sequence different from sequences immediately flanking the subsequence within the full-length nucleic acid sequence, or which subsequence is present in a different arrangement relative to the flanking subsequences from those found in nature. Examples include introns from genes e.g., which are heterologous to the sequences immediately flanking the subsequence, inteins from genes e.g., which are heterologous to the sequences immediately flanking the subsequence, and the like. Examples of cis and trans splicing RNAs and proteins are well known in the art.

Nucleic acids and nucleic acid sequences are "homologous" when they are derived, naturally or artificially, from a common ancestor sequence. During natural evolution, this occurs when two or more descendent sequences diverge from a parent sequence over time, i.e., due to mutation and natural selection. Under artificial conditions, divergence occurs e.g., in one of at least three different general ways.

First, a given sequence can be artificially recombined with another sequence, as occurs, e.g., during cloning or during shuffling methods, e.g., to produce one or more descendent nucleic acids. Second, a nucleic acid can be synthesized de novo, by synthesizing a nucleic acid which varies in sequence from a selected parental nucleic acid sequence. Third, sequences can be modified e.g., in a computer by applying genetic operators which modify a given character string representing a nucleic acid.

When there is no explicit knowledge about the ancestry of two nucleic acids, homology is typically inferred by sequence comparison between two sequences. Where two nucleic acid sequences show sequence similarity it is inferred that the two nucleic acids share a common ancestor. The precise level of sequence similarity required to establish homology varies in the art depending on a variety of factors. For purposes of this disclosure, two nucleic acids are considered homologous where they share sufficient sequence identity to allow direct recombination to occur between the two nucleic acid molecules. Typically, nucleic acids utilize regions of close similarity spaced roughly the same distance apart to permit recombination to occur. The recombination can be in vitro or in vivo. Thus, two non-homologous sequences can be made "homologous" in the methods of the invention by placing homologous insertion sequences into the non-homologous sequences.

Nucleic acids "hybridize" when they associate, typically in solution, or with one of the nucleic acids fixed to a solid support. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology— Hybridization with Nucleic Acid Probes* part I chapter 2 "Overview of principles of hybridization and the strategy of nucleic acid probe assays," Elsevier, N.Y., as well as in Ausubel, supra.

Two nucleic acids "correspond" when they have the same sequence, or when one nucleic acid is a subsequence of the other, or when one sequence is derived, by natural or artificial manipulation from the other.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a sequence comprising a plurality of insertion sequences. For indirect recombination, no more than one of the sequences to be recombined is an actual substrate for recombination.

A collection of "fragmented nucleic acids" is a collection of nucleic acids derived by cleaving one or more parental nucleic acids (e.g., with a nuclease, or via chemical cleavage), or by synthesizing fragments of the one or more parent nucleic acids as oligonucleotides.

A "full-length protein" is a protein having substantially the same domains as a corresponding protein encoded by a natural gene. The protein can have modified sequences relative to the corresponding naturally encoded gene (e.g., due to recombination and selection), but is at least 95% as long as the naturally encoded gene (i.e., has at least 95% of the total number of amino acids as the corresponding naturally encoded gene.)

A "DNAse enzyme" is an enzyme which catalyzes cleavage of a DNA, in vitro or in vivo.

A "nucleic acid domain" is a nucleic acid region or subsequence. The domain can be conserved or not conserved between a plurality of homologous nucleic acids. Typically a domiain is delineated by comparison between two or more sequences, i.e., a region of sequence diversity between sequences is a "sequence diversity domain," while a region of similarity is a "sequence similarity domain." Domain switching" refers to the ability to switch one nucleic acid region from one nucleic acid with a second domain from a second nucleic acid.

A region of "high sequence similarity" refers to a region that is 90% or more identical to a second selected region when aligned for maximal correspondence (e.g., manually or using the common program BLAST set to default parameters). A region of "low sequence similarity" is 40% or less identical to a second selected region when aligned for maximal correspondence (e.g., manually or using BLAST set with default parameters).

A "PCR amplicon" is a nucleic acid made using the polymerase chain reaction (PCR). A "PCR primer" is a nucleic acid which hybridizes to a template nucleic acid and permits chain elongation using a thermostable polymerase under appropriate reaction conditions.

A "library of oligonucleotides" is a set of oligonucleotides. The set can be pooled, or can be individually accessible.

DETAILED DISCUSSION OF THE INVENTION

The present invention provides a variety of new recombination formats and methods for controlling, modulating and tuning recombination rates. In the methods, a plurality of insertion sequences (e.g., about 2, 5, 10, 15, 20, or even more sequences) are integrated into a parental sequence of interest (e.g., in a physical molecule or in a corresponding computer character string). The integration of the insertion sequences alters the hybridization and recombination properties of the resulting molecule relative to the parental molecule and can also be used to influence expression, splicing and/or translation rates of encoded nucleic acids. In addition to integration of insertion sequences, other strategies which modify hybridization and which tune recombination rates can also be used in conjunction with the insertion strategies herein, such as codon modification of the parental nucleic acid to further tune and modify hybridization and/or, e.g., translation. Codon modification strategies are discussed in detail in "SHUFFLING OF CODON ALTERED GENES" by Phillip A. Patten and Willem P. C. Stemmer filed Sep. 28, 19399 e.g. Application No: PCT/US99/22588 and U.S. Ser. No. 09/407,800. This ability to make molecules with altered hybridization and recombination properties is useful for tuning recombination rates. In addition, many nucleic acids are proprietary and the ability to use non-proprietary hybridization altered nucleic acids is of considerable commercial value.

In a preferred embodiment, shuffled recombinant nucleic acids do not hybridize to the parental genes from which they were derived. This is desirable, e.g., where the original protein generates an immune response and a protein with similar functionality but a substantially different primary structure is desired, or, e.g., where the original nucleic acid is proprietary.

INSERTION SEQUENCES

As noted above, an insertion nucleic acid subsequence is a nucleic acid subsequence found in a full-length nucleic acid sequence. The subsequence is derived from a nucleic acid sequence different from sequences immediately flanking the subsequence within the full-length nucleic acid sequence, or which subsequence is present in a different arrangement relative to the flanking subsequences from those found in nature. Most typically, the insertion sequences are derived from nucleic acids which can either be removed from encoded mRNAs (e.g., where the insertion sequences are introns, or are spliced out of DNA by site-specific recombination), or which can be removed from encoded proteins (e.g., by protease-ligation strategies such as intein- extein protein splicing).

Intron/exon strategies

In one common embodiment, the insertion sequences of the invention comprise introns, with the exon regions flanking the sequences comprising sequences of interest. Introns and exons are common, e.g., in eukaryotic nuclear RNA and are also known in bacteria and archaebacteria. See, e.g., Watson et al., *Molecular Biology of The Gene* Fourth Edition, The Benjamin Cummings Publishing Co., Menlo Park, Calif.; Darnell et al., (1990) *Molecular Cell Biology* second edition, Scientific American Books, W.H. Freeman and Company; and Lewin *Genes*, 5th Ed., Oxford University Press (1994). Indeed, a variety of RNA splicing strategies, including those used by cellular machinery and by various vitro mechanisms, including both cis and trans splicing of RNA are well known (in cis reactions a molecule acts on itself, e.g., to achieve splicing (it acts in "cis"); in a trans reaction, a molecule acts on another molecule to achieve a result such as splicing). In addition to Watson and Lewin, id., references describing various forms of RNA splicing include, e.g., Moore et al. (1994) *Cell* 77:805–815; Moore et al. (1993) *The RNA World*, Cold Spring Harbor Laboratory Press; Chow et al. (1977) *Cell* 12:1–8; Berget et al. (1977) *Proc. Natl. Acad. Sci. USA* 74:3171–3175. Moore et al. *Nature* 365:364–368; Roscigno et al. (1993) *J. Biol. Chem.* 268(14):11222–11229; Smith et al. (1989) *Nature* 342:243–247; Konarska et al. (1985) *Cell* 42:165–171; Sutton and Boothroyd (1986) *Cell* 47:527–535; Murphy et al. (1986) *Cell* 47:517–525; Krause and Hirsh (1987) *Cell* 49: 753–761; Bruzik and Steitz (1990) *Cell* 62:889–899; Bruzik (1992) *Nature* 360:692–695 and CHIMERIC RNA MOLECULES GENERATED BY TRANS-SPLICING US. Pat. No. 6,013,487 to Mitchell. Indeed, there is well over 20 years of literature on the topic of introns and RNA splicing; one of skill is presumed to be familiar with this available literature.

In one aspect of the invention, a modified gene sequence comprising insertion sequences is synthesized (by chemical synthesis, recombinantly, by PCR synthetic strategies, or a combination thereof, and/or, e.g., by "virtual" synthesis in a computer). In cases where hybridization to the parental gene is not desirable, the exons in the modified gene sequence are preferably about 24–50 bp in size (such small coding sequences in an intron-exon arrangement are typically referred to as "mini exons"). In nature, mini exons smaller than 50 bp are rare and usually occur as singular mini-exons surrounded by larger exons. Mini exons are also frequently skipped by cellular splicing machinery, for example in a tissue specific fashion, as a from of expression control, e.g., resulting in alternatively spliced products.

To ensure that mini exons in the described modified gene are spliced faithfully, regulatory elements supporting the inclusion of mini exons are included within the introns. These regulatory elements are Intronic Splicing Enhancers (ISEs). For example, a 134 nt ISE found in the chicken cardiac troponin T (cTNT) gene ensures 100% retention of a heterologous 7 nt mini-exon in various cell lines (Carlo et al. (1996) RNA, 2:342–353). An example, cTNT intronic splicing enhancer is:

a a a a t c t c t c t t c t t c t g c c c t c c a t g c c t g g c t g c a g
CAAAGGgtaagtcaggctgcatgCCTCCCACCACACC
TGTGCTGCATGACACCT
GGGGCTGACCTGCAACAGAAGTGGGGCTG
AGGGAAGGACTGTCCTG
GGGACTGGTGTCAGAGC
GGGGTTGGTGACTCTCAGGATGCCCAAAATGCCCA
(SEQ ID NO.: 1).

In another known example of ISEs, two copies of a 105 nt ISE from the c-src oncogene have been shown to stabilize the inclusion of a heterologous mini-exon in a heterologous cell line (Modefferi and Black (1997) *Mol. Cell Biol.* 17:6537–6545). Thus, in one class of embodiments, ISEs are included in some or all of the introns (placement and presence or lack of ISEs can also be used to modulate splicing variations, further increasing sequence diversity in resulting gene products). Variants of the modified gene are evolved, e.g., using DNA shuffling techniques. Resulting genes are typically transfected into cells and selected using appropriate functional assays.

The choice of ISE ensures faithful splicing of a mini exon array. The cTNT ISE is one preferred ISE. The cTNT ISE works in transiently transfected tissue culture cells and in nuclear extracts. It is highly efficient, supporting up to 100% inclusion of a heterologous mini exon in a variety of cells (CHO, NIH 3T3, F9, S3, HELA, COS, M6). Furthermore, in the chicken cardiac troponin T (cTNT) gene, the cTNT ISE stabilizes the inclusion of a constitutively spliced mini exon and tissue specific factors do not appear to be required. In addition, a minimal cTNT ISE of 96 bp has been defined. This synthetic cTNT ISE contains 8 copies of a 7 nt sequence motif separated by spacing sub sequences. The synthetic cTNT ISE supports about 80% inclusion of a heterologous mini exon. When the complete 134 bp ISE is used, the overall intron size can be scaled down to about 170–180 nt. One valuable feature of the cTNT ISE is its position independence. The cTNT ISE supports the inclusion of a mini exon when inserted either upstream or downstream of a mini exon. By including cTNT ISEs in every intron in a non-hybridizing gene homologue, inclusion of each mini-exon is induced by both upstream and downstream ISEs. Thus, a synergistic effect supporting complete splicing of the mini exon array occurs.

In one embodiment, relevant features of chicken cardiac troponin T (cTNT) intronic splicing enhancers include: 1) a 134 nt ISE contains 6 repeats of a 7nt sequence motif, that stabilizes inclusion of a constitutive 6 nt mini-exon in various cell lines, and 2) 8 repeats t96 nt synthetic ISE) which support 80% inclusion of a heterologous mini-exon (7nt).

In another embodiment, the c-src oncogene ISE is used. Relevant features include: 1) a 105 nt ISE. which stabilizes inclusion of a neuron-specific, 18 nt mini-exon, and 2) the c-src ISE is also active in non-neuronal cells: 2 105 nt ISEs induce 78% retention of a heterologous mini-exon in non-neuronal cells.

An exemplar splicing strategy is represented schematically in FIG. 1. As shown, an insertion-modified nucleic acid (e.g., which does not hybridize to a selected non insertion-modified nucleic acid) is transfected into a cell. Following splicing, a spliced gene is produced. The splicing can be either nucleic acid splicing (as depicted) or intein splicing. Common exemplar steps in designing an RNA splicing system can include, e.g., the following: 1) building of splicing constructs; 2) transient transfection of constructs into, e.g., eukaryotic tissue culture cells; 3) isolation of RNA, RT-PCR splicing products; 4) sequencing of splicing products; 5) putting splicing products into expression vectors and 6) testing chimeric gene products in functional assays.

Figure 2:
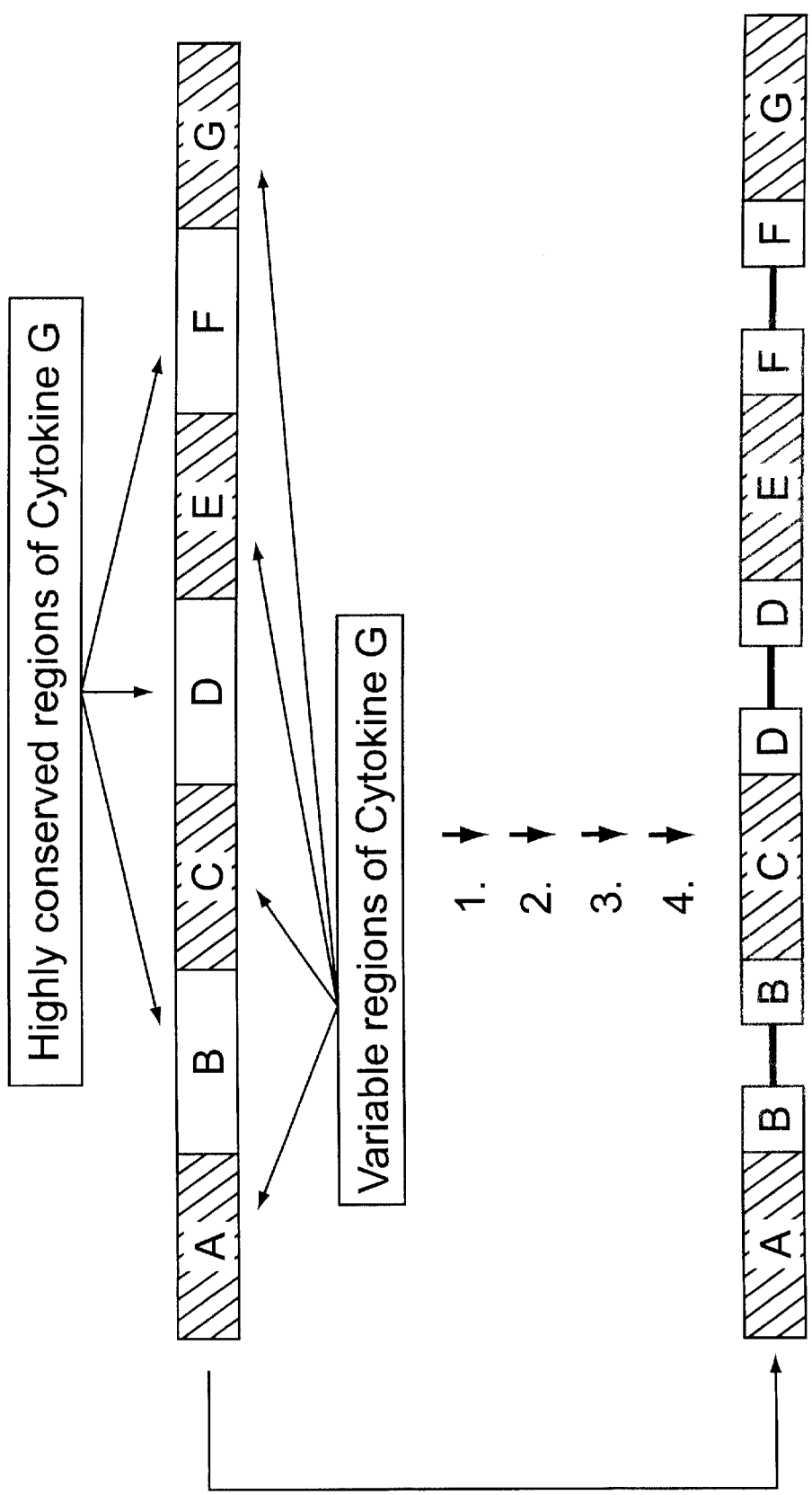
FIG. 2 is a schematic of an exemplar shuffling strategy for Cytokine G, an arbitrarily designated cytokine.

An example of this strategy is schematically described in FIG. 2 for an example cytokine, arbitrarily designated "cytokine G." Cytokines generally include, e.g., interleukins, interferons, chemokines, hematopoietic growth factors, tumor necrosis factors, transforming factors and the like. In general, these proteins are small molecular weight proteins that regulate maturation, activation, proliferation and/or differentiation of cells, e.g., of the immune system. Because, e.g., of the convenient size and relative commercial value of these proteins, cytokines represent a preferred target of the present invention. As shown, in step 1, maximum divergence from an initial cytokine type (e.g., the human form of cytokine G) is obtained by performing shuffling (e.g., in vitro, in vivo or in silico), e.g., by performing family shuffling. In step 2, introns are inserted into conserved regions and shuffling is performed to optimize splicing of the resulting nucleic acids. In step 3, translation is selected for, e.g., by FACS or other appropriate methods. In step 4, functional non-hybridizing nucleic acids (i.e., which do not hybridize to the initial cytokine G type) are isolated.

In the case of an exemplar 500 bp coding sequence, a non-hybridizing gene comprising 24 bp exons has a total size using the cTNT ISE intron arrangement discussed herein of about 3920 bp. Many genes of interest encode polypeptides in this approximate size range, including the genes for insulin proteins, peptide hormones, cytokines, epidermal growth factors, fibroblast growth factors, hepatocyte growth factors, insulin-like growth factors, interferons, interleukins, keratinocyte growth factors, leukemia inhibitory factors, oncostatin M, PD-ECSF, pleiotropin, SCF, c-kit ligand, VEGFs (VEGEF has a number of well-characterized splice variants with different activities), G-CSF, GM-CSF, many oncogene and tumor suppressor encoded peptides, plant hormones, disease resistance proteins, some bacterial proteins, some proteases, peptide ligands, angiogenisis inhibitors, C-X-C chemokines, C—C chemokines, cystein knot proteins (such as TGFβ, NGF, PDGFβ, etc.), Rnases and many others.

To facilitate assembly of the non-hybridizing gene, the introns can include suitable restriction sites or other features for sequence assembly. For example, in one embodiment, the gene is assembled from units consisting of a mini exon flanked by 2 intron halves.

A variety of variations can be performed to modify the efficiency of this system. For example, ISE sequences and trans acting splicing factors can be shuffled to improve (or decrease, if desired) the efficiency of the mini-exon array. For this purpose, cTNT ISE sequences and genes encoding splicing factors from different species are isolates and subjected to shuffling. Structured introns can be used to guide splicing.

Similarly, the cell line can be selected for optimum splicing. Indeed, the cell line can be evolved, e.g., by whole genome shuffling as taught in Del Cardayre et al. 09/116,188 "EVOLUTION OF WHOLE CELLS AND ORGANISMS BY RECURSIVE SEQUENCE RECOMBINATION" filed Jul. 15, 1998 to optimize splicing for a particular ISE. Thus, either the ISE, or the cell line, or both, can be optimized for splicing prior to use in a particular gene.

Properly spliced sequences can be detected by detecting splicing products such as nucleic acids (e.g., by RT-PCR amplification), and proteins (e.g., by expressing gene products on the surface of cells and panning for particular epitopes, e.g., by ligand panning or FACS). For PCR amplification strategies, either those that rely on downstream analysis (e.g., gel electrophoresis, sequencing of products and the like) or those that rely on real time methods (e.g., FRET, Taqman, molecular beacons or the like), or both can be used. Phage display can also be used, as can polysome display.

Splice site consensus sequences extend for 1–2 nucleotides into exons at both the 5' and 3' ends. However, only the G residue at the 3' end of the exon is strongly conserved ragout 79%). The other positions are more flexible (30–60%). Thus, by shuffling splice site sequences and using wobble positions at the 3' end of exons, introduction of efficient splice sites into the coding sequences is optimized.

Bacterial self splicing introns and trans splicing introns can also be used.

Protein Splicing

Analogous to RNA splicing approaches, the coding sequence of a gene can also be interrupted by integration of insertion sequences which encode one or more intein. Inteins, sometimes referred to as "intervening protein sequences", (Perler, et al., Nucleic Acids Research, 22:1125–1127 (1994)) or as "protein introns," "protein spacers," "protein inserts" or the like, are genetic elements that are eliminated from protein sequences to produce mature (typically functional) proteins. In other words, the proteins of intein interrupted genes are expressed as precursor proteins (and can be expressed as one or as more than one protein chain). Upon protein splicing, the inteins are removed to generate a functional protein.

Inteins were discovered, e.g., in yeast genes (Kane, et al., Science, 250:651–657 (1990)); Hirata, et al., J. Biol. Chem., 265:6726–6733 (1990)) for the vacuolar ATPase VMA1 gene of *Saccharomyces cerevisiae*. Since then, many more cases of protein splicing have been found (reviewed, e.g., in Clyman, ASM News, 61:344–347 (1995); Colston and Davis, Mol. Microbiol., 12:359–363 (1994)). Inteins have been found in eukaryotes, bacteria and archaebacteria, i.e., in all kingdoms. Inteins are sometimes described as protein sequences which are embedded, typically in frame, within a precursor protein, and which are removed by protein splicing. During the protein splicing process, two terminal polypeptide portions become ligated by a peptide bond, and form a "fusion protein" which corresponds to one or more extein. The amino acids found at two hexapeptide motifs on each end of a typical intein influence the splicing process. These regions, which are also called intein splice sites, are somewhat conserved in inteins. The mechanism of protein splicing involves several of these amino acids, typically including, e.g., the C-terminal histidine, asparagine and cysteine/threonine/serine residues (Davis, et al., *J. Bacteriol.*, 173:5653–5662 (1992); Hirata and Anraku, *Biochem. Biophy. Res. Comm.*, 188:40–47 (1992); Hodges, et al., *Nucleic Acids Research*, 20:6153–6157 (1992); Cooper, et al., *EMBO Journal*, 12:2575–2583 (1993)).

A "native" intein activity is one which occurs, in vitro or in vivo, as a result of activity of proteins or other cellular factors participating in a splicing reaction. For example, Splicing can be autocatalytic (a cis reaction) and, at least in this mode, typically does not require host cell cofactors, as inteins can splice out of their precursor proteins in a variety of in vivo and vitro expression systems, including simple phosphate buffered saline (Davis, et al., J. Bacteriol., 1–3:5653–5662 (1992); Xu, et al., Cell, 75:1371–1377 (1993); and reviewed in Colston and Davis, Mol. Micobiol., 12:359–363 (1994)). In addition to such native or "spontaneous" intein splicing activity, "controllable" intein splicing has also been proposed, in which artificial exposure to unusual levels of heat or light, or artificial dephosphorylation or deglycosylation of proteins, or artificial treatment with chemical reagents is used to control intein splicing reactions. See, e.g., Comb et al. U.S. Pat. No. 5,834,247 and U.S. Pat. No. 5,496,714. Either native or controllable intein splicing can be used in the context of the present invention. In addition to intein splicing, chemical splicing of oligopeptides to form active proteins can also be performed in the context of the present invention.

Relevant features of inteins and intein splicing, as well as certain forms of chemical ligation of polypeptides, are described in the abundant literature on the topics, including: Clarke (1994) "A proposed mechanism for the self-splicing of proteins" *Proc. Natl. Acad. Sci. USA* 91:11084–11088; Clyman (1995) "Some Microbes have splicing proteins" *ASM News* 61:344–347; Colston and Davis (1994) "The ins and outs of protein splicing elements" *Molecular Microbiology* 12, 359–363; Cooper et al. (1993) "Protein splicing of the yeast TFP1 intervening protein sequence: a model for self-excision" *EMBO J.* 12:2575–2583; Cooper and Stevens (1993) "Protein splicing: Excision of intervening sequences at the protein level" *BioEssays* 15, 667–673; Cooper and Stevens (1995) "Protein splicing: Self-splicing of genetically mobile elements at the protein level" *TIBS* 20, 351–357: Cook et al. (1995) "Photochemically initiated protein splicing" *Angew. Chem. Int. Ed. Engel* 34, 1620–1630; Dalgaard, J. (1994) "Mobile introns and inteins: friend or foe?" *Trends Genet* 10, 306–7; Davis et al. (1992) "Protein Splicing in the Maturation of M. Tuberculosis RecA Protein: A Mechanism for Tolerating a Novel Class of Intervening Sequence" *Cell* 71:201–210; Davis et al. (1991) "Novel Structure of the recA Locus of Mycobacterium tuberculosis Implies Processing of the Gene Product" *J. Bacteriol.* 173:5653–5662; Davis et al. (1994) "Evidence of selection for protein introns in the RecAs of pathogenic Mycobacteria" *EMBO J.* 13, 699–703; Davis et al. (1995) "Protein splicing—the lengths some proteins will go to" *Antonie Van Leeuwenhoek* 67:131–137; Doolittle, (1993) "The comings and goings of homing endonucleases and mobile introns" *Proc. Natl. Acad. Sci USA*. 90:5379–5381; Doolittle and Stoltzfus (1993) "Genes-in-pieces revisited" *Nature* 361 :403; Hirata and Anraku (1992) "Mutations at the Putative Junction Sites of the Yeast VMA1 Protein, the Catalytic Subunit of the Vacuolar Membrane H+-ATPase, Inhibit its Processing by Protein Splicing" *Biochem. Biophys. Res. Comm.* 188:40–47; Hirata et al. (1990) "Molecular Structure of a Gene, VMA1, Encoding the Catalytic Subunit of H+-Translocating Adenosine Triphosphatase from Vacuolar Membranes of Saccharomyces cereviaiae" *J. Biol. Chem.* 265, 6726–6733; Hodges et al. (1992) "Protein splicing removes intervening sequences in an archaea DNA polymerase" *Nucleic Acids Res.* 20:6153–6157; Kane et al. (1990) "Protein Splicing Converts the Yeast TFP1 Gene Product to the 69-kD Subunit of the Vacuolar H+-Adenosine Triphosphatase" *Science* 250:651–657; Koonin (1995) "A protein splice-junction motif in hedgehog family proteins" *Trends Biochem. Sci*. 20:41–142; Kumar et al. (1996) "Functional characterization of the precursor and spliced forms of recA protein of Mycobacterium tuberculosis" *Biochemistry* 35:1793–1802, and Kawasaki, M., et al., Biochemical and Biophysical Research Communications, vol. 222, "Folding-dependent in vitro protein splicing of the Saccharomyces cerevisiae VMA1 protozyme", pp. 827–832, 1996. Gimble and Thomner (1992) *Nature* 357:301–306; Gimble and Thorner (1993) *J. Biol. Chem.*, 268:21844–21853; Pietrovski (1996) "A new intein in cyanobacteria and its significance for the spread of inteins" *Trends in Genetics* 12:287–288; Shao et al. (1996) "Proteins splicing: Evidence for an N—O acyl rearrangement as the initial step in the splicing process" *Biochemistry*, 35:3810–3815; Shub and Goodrich-Blair (1992) *Cell*, 71:183–186; WO 98/49274; WO 98/49275; WO 98/40394; WO 99/11655; WO 96/34878; WO 98/28434Kent et al. U.S. Pat. No. 5,910,437; Dawson et al. 5,891,993; and Jocbs et al., U.S. Pat. No. 5.981,182.

Additional details on protein splicing generally can be found at the Intein Databases web site (www.neb.com/neb/inteins/intein_intro.html); and in, e.g., *Nucleic Acids Research* 26(7):1741–1758.

Minimal functional inteins lacking a homing endonuclease have been defined. For example, a semi-synthetic intein 135 aa in length undergoes 50–90% intein removal in vitro (Lew et al. (1998) JBC 273:15887–15890). In the context of the present invention, inteins are optionally optimized by forced evolution (e.g., using shuffling) to achieve optimal protein splicing in any desired heterologous context. Selection of protein products is performed using an appropriate functional or physical assay for the protein.

Figure 4:
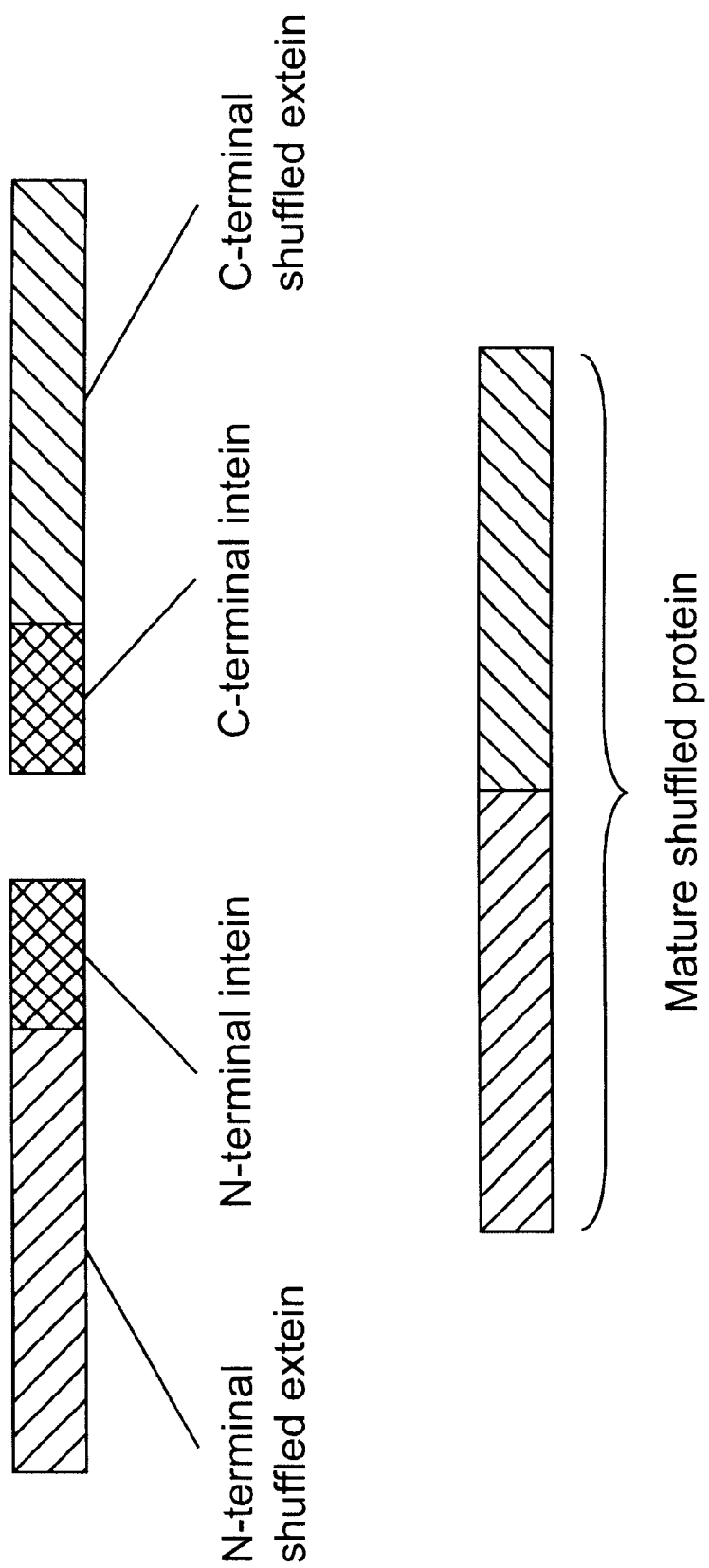
FIG. 4 is a schematic of a trans-splicing library strategy.

In addition to cis-splicing of inteins, trans-splicing of inteins is also used in the present invention (as noted above, both cis and trans splicing of RNA can also be used to produce insertion modified nucleic acids). In one embodiment, proteins of interest are encoded by two or more separate nucleic acids which are expressed to produce two separate polypeptides. These two or more separate polypeptides are recombined to form the protein of interest. This is illustrated in FIG. 4. This figure shows screening of libraries encoded by split exteins that are trans-spliced. The gene family to be shuffled is divided into two (or more) exteins. Trans-splicable inteins are put between the exteins. Libraries of N- and C-terminal exteins fused to their respective inteins are constructed by standard methods. The protein fragments are expressed either in the same or in different cells. Trans splicing is promoted either in vivo or in vitro to yield a mature shuffled protein that is generated without the manipulation at any step of full length mature shuffled genes. Examples of trans-intein splicing systems are available, such as the DnaE gene, encoded by dnaE-n and dnaE-c in the Syidcilocystis sp. PCC6803 genome. These and other systems can be shuffled to optimize splicing in general (including trans splicing), or in any specific system of interest.

In general, it is sometimes desirable to produce proteins which are not expressed in an active format. This is because, for example, some proteins are toxic to the cell in which the protein is expressed (e.g., RNases, DNases, toxins such as ricin, proteases, apoptosis inducing factors, microtubule proteins, etc.). In these situations, it is advantageous to express a protein in an inactive form that can be conditionally activated (e.g., by splicing of two inactive peptides to form an active protein, or by trans-splicing of RNAs to produce a coding nucleic acid). It is also possible to express different segments of the nucleic acid and/or protein in different systems (e.g., where expression is biased in one or more cell), e.g., to express different portions of the nucleic acids or proteins in different cells, or even in different in vitro expression systems. Thus, for example, one can express a portion of a protein in an *E. coli* and a portion in yeast. The separate portions are contacted and allowed to undergo trans-splicing. In some circumstances, it is convenient from a production standpoint to produce and store one portion of a protein or nucleic acid to be spliced and then to separately produce another portion at a different time. After the relevant portions are produced, they are combined, in vitro or in vivo, and the final product produced.

In addition, separate expression of protein fragments is useful for combinatorial purposes, i.e., the fragments can be separately evolved and the ability to recombine different fragments can increase the diversity in the final proteins which result from the splicing reactions. For example, the viability, activity and folding of proteins can be influenced by multiple regions of the protein, often simultaneously or in a cooperative fashion. By removing these cooperative effects until after the initial expression of protein fragments, these effects can be avoided or advantageously modulated. Thus, generally, separate large libraries of diversity can be generated and "recombined" by splicing the protein fragments encoded by the library members.

As an example, one of skill can transform mammalian cells with a library of "split gene" fragment members (i.e., encoding portions of a protein of interest) to generate large libraries of cells encoding a spliced proteins of interest. For example, the number of cells that can be transfected in a typical DNA transfection experiment is generally a limiting feature in mammalian transfection/screening/cloning applications. For example, one might obtain only about 1000 stable transfectants following transfection of a population of cells with a library of $10^9$ different DNAs. However, using the present invention, one can sample much more than 1000 shuffled proteins by transfection, such that the typical transfectant receives 10 shuffled N-terminal and 10 shuffled C-terminal exteins. Each cell is then capable of making 100 unique trans-spliced mature proteins. This gives a large increase in the number and diversity of resulting recombined genes that can then be expressed and screened. It will be appreciated that the use of more than two fragments to generate the spliced protein of interest provides even larger numbers of resulting spliced proteins.

Figure 5:
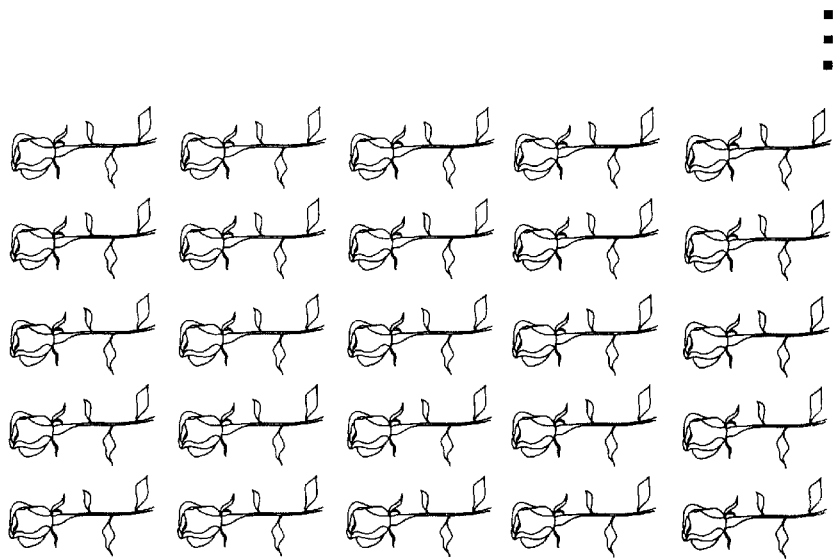
FIG. 5 is a schematic of a combined trans-splicing/classical breeding approach to making a library, using roses as an example plant.
Figure 5:
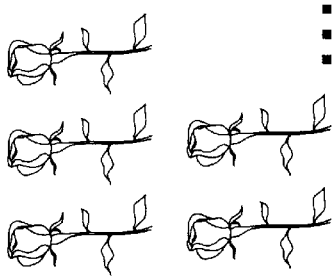
Figure 5:
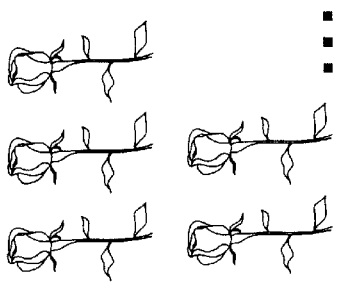

There is a large class of screening problems that are best performed in whole organisms, as there are not necessarily good in vitro or cellular assays for the activity of interest. For example, insect or herbicide resistance in plants or shuffled growth hormones in animals are advantageously screened in the plant or animal for which the activity is to be developed. Advantageously, an example of the "split" gene strategy embodied by the use of trans-splicing proteins is the screening of shuffled split gene libraries in whole organisms, e.g., for the development of these activities in the plant or animal of interest. In particular, using the split gene method, it is possible to access and screen diversity equal to (at least) the square of the number of transgenic organisms. For example, if 100 transgenic plants expressing 100 different shuffled N-terminal exteins are crossed to 100 transgenic plants expressing 100 different C-terminal exteins (e.g., by classical breeding) $10^4$ transgenic plants with unique spliced shuffled proteins will result upon splicing of the different N- and C-terminal portions of the proteins in the plants. This approach is illustrated schematically in FIG. 5 (only limited sets old breeding plants and progeny are represented for clarity of illustration) for sets of roses (any plant can be substituted for the roses which are depicted). For clarity of illustration, the complete sets are not shown. As depicted, e.g., 100 transgenic plants expressing 100 different shuffled N-terminal exteins are crossed to 100 transgenic plants expressing 100 different C-terminal exteins (e.g., by classical breeding), producing $10^4$ transgenic plants with unique spliced shuffled proteins in the F1 generation. See also, Patten et al. "ENCRYPTION OF TRAITS USING SPLIT GENE SEQUENCES AND ENGINEERED GENETIC ELEMENTS" U.S. Ser. No. 60/164,618 Filed Nov. 10, 1999.

One of skill will appreciate that, here again, fragmentation of the protein of interest into more than two extein fragments and the creation of libraries of organisms expressing each extein fragment (e.g., a C-terminal fragment, one or more middle fragment(s) and an N-terminal fragment) provides even larger numbers of proteins which can result from classical breeding of the different organism library members.

In addition to using intein-extein strategies to evolve proteins of interest, the present invention also provides methods and libraries for improving splicing activity. In particular, sequences encoding inteins and exteins can be shuffled (e.g., using any available shuffling method as set forth herein) and the splicing activity of the resulting shuffled sequences assessed, e.g., by assaying for a resulting spliced product (in this embodiment, splicing can be either cis or trans splicing). For example, the spliced product can encode a catalytic or other activity that can be measured using standard methods (e.g., in an assay which produces a detectable signal such as luminescence, fluorescence, or the like which is dependent on the presence of the spliced protein).

Site Specific Recombination

In site-specific recombination strategies, in vivo recombination is carried out to remove insertion sequences. In one aspect, enzymes carrying out site specific recombination are evolved by shuffling methods which select for increased performance and specificity. Selection of functional products is performed by detecting, e.g., mRNA or protein products, or by using an appropriate functional assay. Evolved variants of site-specific recombinases have acquired specificity for novel DNA recombination signals (e.g., altered loxP sites), so that the modified sites (e.g., lox P sites) encode a protein of interest.

Alternative Splicing

Alternative splicing of pre-mRNAs is used in cells to recombine functional gene segments encoded by separate exons. In the present invention, shuffling of protein domains or domains of non coding functional RNAs (viral RNAs, snRNAs, tRNAs, rRNAs, gRNAs, etc.) is performed based upon alternative splicing techniques. Synthetic genes containing multiple exons derived from related or unrelated (or distantly related) genes separated by introns are created. In one embodiment, alternative splicing is induced by transient transfection of the genes into, e.g., eukaryotic cells. Transiently transfected cells accomplish alternative splicing very efficiently and stable cell lines are not necessary. Although in vitro splicing of RNAs up to about 1 kb in size is possible in nuclear extracts, in vitro splicing is relatively inefficient, especially when alternative splicing is desired. Interesting splicing products are assayed by functional assays or by detection of RNAs (e.g., by RT-PCR) or translated proteins. Splicing products are optionally recovered by RT-PCR, cloned and sequenced or further assayed. Splicing products of interest are, e.g., introduced into expression systems and gene products tested in functional assays.

The goal of domain recombination by alternative splicing is to create a large number of recombinant molecules without disrupting functional domains. The design of synthetic genes subjected to alternative splicing is optimized to achieve this goal.

The design of synthetic genes allows for modulation of patterns of splicing. Creating pre-mRNAs with e.g., about 6–20 exons provides many different exon combinations in spliced products. An even higher frequency of alternatively spliced RNAs occurs if mini exons are included. Exons smaller than 50 bp are inefficiently recognized (absent an ISE as discussed above) by the splicing machinery and as a consequence, are often skipped. Employing multiple mini exons induces exon skipping, creating additional splicing diversity.

Figure 3:
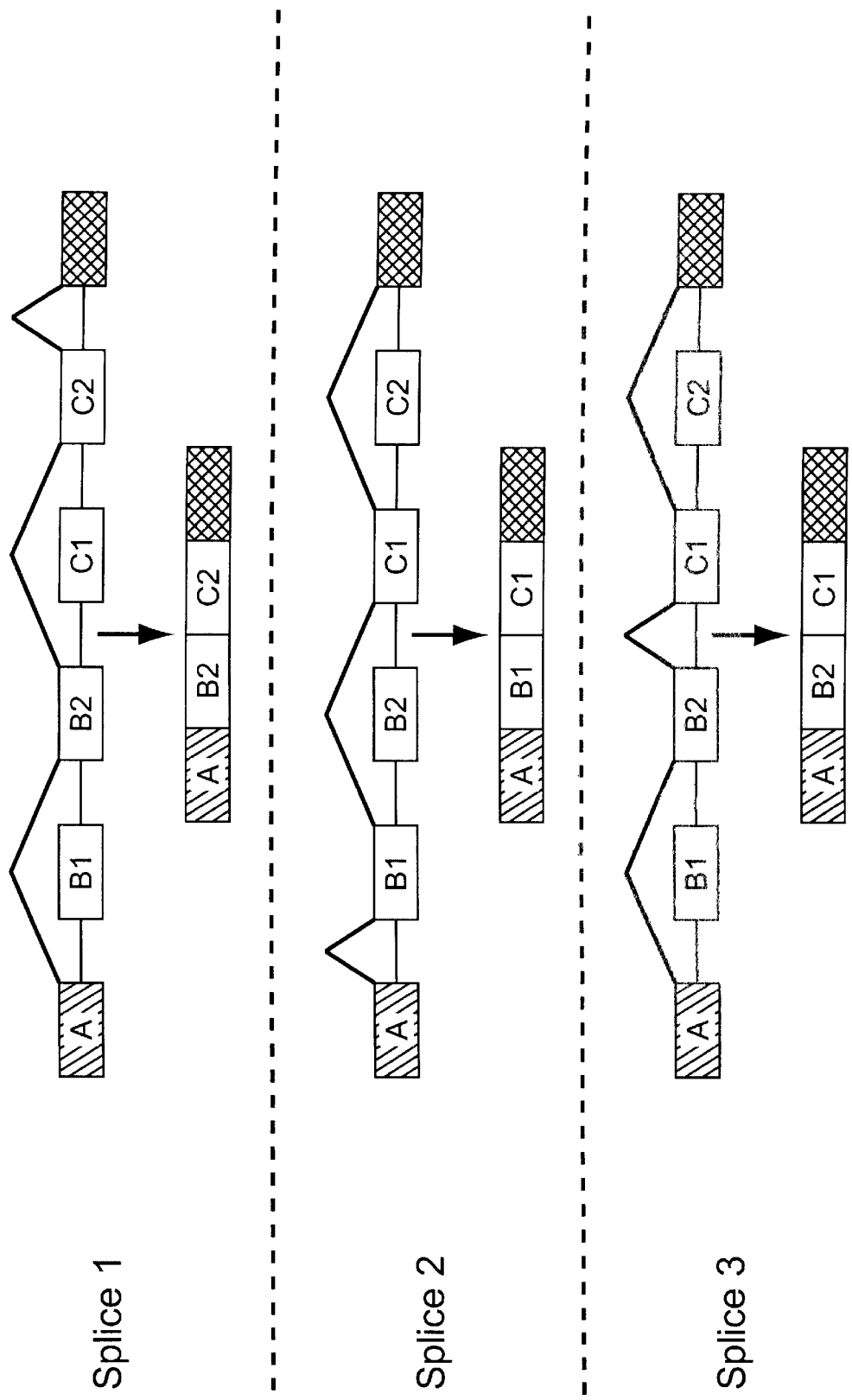
FIG. 3 is a schematic of a domain shuffling strategy.

An example of a synthetic gene undergoing multiple patterns of splicing is shown in FIG. 3. Exons are designated A, B and C and encode unrelated functional domains. B1 and B2 encode variants of the same functional domain, or for spacer regions. C1 and C2 encode variants of another functional domain. Exon 3 includes a polyadenylation site.

In addition to inducing exon skipping, selected exons can also be enriched in splicing products through the use of splicing enhancers. For example, purine rich sequence elements such as the sequence GAR, where R is a purine have been found within exons. These splicing enhancers activate the use of the upstream 3' splice site, thus stabilizing the exon in which thee are located. Purine rich splicing enhancers are found in genes from many higher eukaryotes and function in many tissues and cell lines. Incorporating splicing enhancers allows for anchoring of exons in a splicing product, preventing it from being skipped (which is especially desirable where combinations of the domain encoded by the exon with other domains is desirable). This biasing of splicing during recombination is a feature of the invention.

Flexible spacer regions between exons can also be used to increase the functionality of chimeric molecules.

MAKING INSERTION SEQUENCES AND GENES

As noted above, insertion sequences and nucleic acids comprising insertion sequences are made according to standard recombinant or synthetic methods, optionally in combination with shuffling or PCR synthetic methods. Generally, in silico, chemical synthetic, ligase and/or polymerase mediated approaches to synthesis are optionally performed to produce insertion modified nucleic acids.

In addition to the references noted elsewhere herein, general texts which describe molecular biological techniques useful herein, including mutagenesis, library construction, screening assays cell culture and the like include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.)., Vol. 1–3, Cold Spring Harbor Laboratory, Cold Spring Harbor, N.Y., 1989 ("Sambrook") and *Current Protocols in Molecular Biology*, F.M. Ausubel et al., eds., Current Protocols, a joint venture between Greene Publishing Associates, Inc. and John Wiley & Sons, Inc., (e.g., supplemented through 1999) ("Ausubel")).

Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley-Liss, New York (1994)) and the references cited therein, Humason (*Animal Tissue Techniques*, fourth edition W.H. Freeman and Company (1979)) and Ricciardelli, et al., *In Vitro Cell Dev. Biol.* 25:1016–1024 (1989). References for plant cell cloning, culture and regeneration include Payne et al. (1992) *Plant Cell and Tissue Culture in Liquid Systems* John Wiley & Sons. Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS).

In addition to the references noted supra, a variety of purification/protein folding methods for expressing encoded proteins are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, $2^{nd}$ *Edition* Wiley-Liss, N.Y.; Walker (1996) *The Protein Protocols Handbook* Humana Press. N.J., Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ *Edition* Springer Verlag, N.Y.; Janson and Ryden (1998) *Protein Purification: Principles, High Resolution Methods and Applications, Second Edition* Wiley-VCH, N.Y.; and Walker (1998) *Protein Protocols on CD-ROM* Humana Press, N.J.; and the references cited therein.

Examples of techniques sufficient to direct persons of skill through in vitro amplification methods, useful e.g., for amplifying oligonucleotide shuffled nucleic acids or for reassembly of nucleic acids comprising insertion sequences, include the polymerase chain reaction (PCR) the ligase chain reaction (LCR), Qβ-replicase amplification and other RNA polyrnerase mediated techniques (e.g., NASBA). These techniques are found in Berger, Sambrook, and Ausubel, id., as well as in Mullis et al., (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990) *C&EN* 36–47; *The Journal Of NIH Research* (1991) 3, 81–94; Kwoh et al. (1989) *Proc. Natl. Acad. Sci. USA* 86, 11173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426, 039. Improved methods of amplifying large nucleic acids by PCR are summarized in Cheng et al. (1994) *Nature* 369:684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

In one preferred method, assembled sequences are checked for incorporation of insertion sequences. This can be done by cloning and sequencing the nucleic acids, and/or by restriction digestion, e.g., essentially as taught in Sambrook, Berger and Ausubel, above. The extent of PCR amplification can also be determined by incorporation of a label into one or more amplified elongated nucleic acid, or by hybridization to relevant probes, e.g., in a fluorogenic 5' nuclease assay, TaqMan, FRET, use of molecular beacons (or other real time PCR analysis methods), etc. In addition, sequences can be PCR amplified and sequenced, directly or indirectly. Thus, in addition to, e.g., Sambrook., Berger, Ausubel and Innis (id. and above), additional PCR sequencing PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):161 1–1617). In the methods, 4 PCR reactions on a template are performed, in each of which one of the nucleotide triphosphates in the PCR reaction mixture is partially substituted with a 2'deoxynucleoside 5'-[P-borano]-triphosphate. The boronated nucleotide is stochastically incorporated into PCR products at varying positions along the PCR amplicon in a nested set of PCR fragments of the template. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it uses fewer biochemical manipulations than performing standard Sanger-style sequencing of PCR amplicons. Again, real time PCR analysis (FRET, molecular beacons, etc.) provide a simple method for assessing sequences.

Codon Modification

In one aspect, the genes utilized in the methods herein have altered codon use as compared to the parental sequences from which the genes are derived. In particular, it is useful, e.g., to modify codon preference to optimize expression in a cell in which a recombinant product of an oligonucleotide shuffling procedure is to be assessed or otherwise selected. Conforming a recombinant nucleic acid to the codon bias of a particular cell in which selection is to take place typically results in maximization of expression of the recombinant nucleic acid. Because the oligonucleotides used in the various strategies herein typically are made synthetically, selecting optimal codon preference is done simply by reference to well-known codon-bias tables.

In addition to selection of oligonucleotide sequences to optimize expression, codon preference can also be used to increase sequence similarity between distantly related nucleic acids which are to be recombined. By selecting which codons are used in particular positions it is possible to increase the similarity between the nucleic acids, which, in turn, increases the frequency of recombination between the nucleic acids. Additional details on codon modification procedures and their application to DNA shuffling are found in "SHUFFLING OF CODON ALTERED GENES" by Patten et al. filed Sep. 28, 1999, U.S. Ser. No. 09/407,800.

Expression in Vitro

Although often discussed herein in terms of cellular expression, the nucleic acids produced by the various procedures herein can be expressed in vivo or in vitro. Thus, in one embodiment of the invention, nucleic acids produced by the various diversity generation methods set forth herein (insertion of introns, inteins, or the like, optionally in combination with shuffling, mutation, or the like) are transcribed (i.e., where the nucleic acids are DNAs) into RNA, spliced if appropriate and translated into proteins (which can undergo splicing as discussed herein), which are, optionally, screened by any appropriate assay. Common in vitro transcription and/or translation reagents include reticulocyte lysates (e.g., rabbit reticulocyte lysates) wheat germ in vitro translation (IVT) mixtures, E. coli lysates, canine microsome systems, HeLa nuclear extracts, the "in vitro transcription component," (see, e.g., Promeca technical bulletin 123), SP6 polymerase, T3 polymerase, T7 R.N.A polymerase (e.g., Promega #TM045), the "coupled in vitro transcription/translation system" (Progen Single Tube Protein System 3) and many others. Many of translation systems are described, e.g., in Ausubel, supra. as well as in the references below, and many transcription/translation systems are commercially available.

Generally, cell-free transcription/translation systems can be employed to produce polypeptides from solid or liquid phase sets of DNAs or RNAs. Several transcription/translation systems are commercially available and can be adapted to the present invention by the appropriate addition of transcription and or translation reagents to insertion-modified nucleic acids. A general guide to in vitro transcription and translation protocols is found in Tymms (1995) *In vitro Transcription and Translation Protocols: Methods in Molecular Biology* Volume 37, Garland Publishing, NY. Several in vitro transcription and translation systems are well known and described in Tymms (1995), id. For example, an untreated reticulocyte lysate is commonly isolated from rabbits after treatment of the rabbits with acetylphenylhydrazine as a cell-free in vitro translation system. Similarly, coupled transcription/translation systems often utilize an E. coli S30 extract. See also, the Ambion 1999 Product Catalogue from Ambion, Inc (Austin, Tex.). A variety of commercially available in vitro transcription and translation reagents are commercially available, including the PROTEINscilpt-PRO™ kit (for coupled transcription/ translation) the wheat germ IVT kit, the untreated reticulocyte lysate kit (each from Ambion, Inc (Austin, Tex.)), the HeLa Nuclcar Extsract in vitro Transcription system, the TnT Quick coupled Transcription/translation systems (both from Promega, see, e.g., Technical bulletin No. 123 and Technical Manual No. 045), and the single tube protein system 3 from Progen. Each of these available systems (as well as many other available systems) have certain advantages which are detailed by the product manufacturer.

In addition, the art provides considerable detail regarding the relative activities of different in vitro transcription translation systems, for example as set forth in Tymms, id.; Jermutus et al. (1999) "Comparison of *E. Coli* and rabbit reticulocyte ribosome display systems" *FEBS Lett.* 450 (1–2): 105–10 and the references therein; Jermutus et al. (1998) "Recent advances in producing and selecting functional proteins by using cell-free translation" *Curr. Opin. Biotechnol.* 9(5):534–48 and the references therein; Hanes et al. (1988) "Ribosome Display Efficiently Selects and Evolves High-Affinity Antibodies in vitro from immune Libraries" *PNAS* 95:14130–14135 and the references therein; and Hanes and Pluckthun (1997) "In vitro Selection and Evolution of Functional Proteins by Using Ribosomc Display." *Biochemistry* 94:4937–4942 and the references therein.

For example, an untreated rabbit reticulocyte lysate is suitable for initiation and translation assays where the prior removal of endogenous globin mRNA is not necessary. The untreated lysate translates exogenous mRNA, but also competes with endogenous mRNA for limiting translational machinery.

Similarly, The PROTEINscript-PRO™ kit from Ambion is designed for coupled in vitro transcription and translation using an *E. coli* S30 extract. In contrast to eukaryotic systems, where the transcription and translation processes are separated in time and space, prokaryotic systems are coupled, as both processes occur simultaneously. During transcription, the nascent 5'-end of the mRNA becomes available for ribosome binding, allowing transcription and translation to proceed at the same time. This early binding of ribosomes to the mRNA maintains transcript stability and promotes efficient translation. Coupled transcription: translation using the PROTEINscript-PRO Kit is based on this *E. coli* model.

The Wheat Germ IVT™ Kit from Ambion, or other similar systems, is/are a convenient alternative, e.g., when the use of a rabbit reticulocyte lysate is not appropriate for in vitro protein synthesis. The Wheat Germ IVT™ Kit can be used, e.g., when the desired translation product comigrates with globin (approx. 12–15 kDa), when translating mRNAs coding for regulatory factors (such as transcription factors or DNA binding proteins) which may already be present at high levels in mammalian reticulocytes, but not plant extracts, or when an mRNA will not translate for unknown reasons and a second translation system is to be tested.

The TNT® Quick Coupled Transcription/Translation Systems (Promega) are single-tube, coupled transcription/translation reactions for eukaryotic in vitro translation. The TNT® Quick Coupled Transcription/Translation System combines RNA Polymerase, nucleotides, salts arid Recombinant RNasin® Ribonuclease Inhibitor with the reticulocyte lysate to form a single TNT® Quick Master Mix. The TNT® Quick Coupled Transcription/Translation System is available in two configurations for transcription and translation of gene cloned downstream from either the T7 or SP6 RNA polymerase promoters. Included with the TNT® Quick System is a luciferase-encoding control plasmid and Luciferase Assay Reagent which can be used in a non-radioactive assay for rapid (<30 seconds) detection of functionally active luciferase protein.

Many other systems are well known, well characterized and set forth in the references noted herein, as well as in other references known to one of skill. It will also be appreciated that one of skill can produce transcription/translation systems similar to those which are commercially available from available materials, e.g., as taught in the references noted above.

DIVERSITY GENERATION STRATEGIES

The present invention makes use of shuffling and other diversity generation methods to recombine, mutate, or otherwise create or diversify insertion modified nucleic acids. Nucleic acids produced by the methods herein are optionally subjected to shuffling or other diversity generation methods (e.g., mutagenesis) to improve or modify the encoded function of the nucleic acids. For example, insertion sequences can be shuffled, e.g., by family shuffling techniques (e.g., family shuffling of homologous introns), mutated or otherwise diversified.

A variety of diversity generating protocols, including nucleic acid shuffling protocols, including family shuffling protocols, are available and fully described in the art. The following publications describe a variety of recursive recombination procedures and/or methods which can be incorporated into such procedures, as well as other diversity generating protocols: Stemmer, et al., (1999) "Molecular breeding of viruses for targeting and other clinical properties." *Tumor Targeting* 4:1–4; Nesset al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438: Zhang et al. (1997) "Directed evolution of an effective fucosidase from a galactosidase by DNA shuffling and screening" *Proceedings of the National Academy of Sciences, U.S.A.* 94:4504–4509; Patten et al. (1997) "Applications of DNA Shuffling to Pharmaceuticals Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255:373–386; Stemmer (1996) "Sexual PCR and Assembly PCR" In: *The Encyclopedia of Molecular Biology*. VCH Publishers, New York. pp.447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxyribonucleotides" *Gene*, 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proceedings of the National Academy of Sciences, U.S.A.* 91:10747–10751.

Additional details regarding DNA shuffling and other diversity generating methods are found in U.S. Patents by the inventors and their co-workers, including: U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;" U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "METHODS AND COMPOSITIONS FOR CELLULAR AND METABOLIC ENGINEERING."

In addition, details and formats for DNA shuffling and other diversity genes sting protocols are found in a variety of PCT and foreign patent application publications, including: Stemmer and Crameri, "DNA MUTAGENESIS BY RANDOM FRAGMENTATION AND REASEMBLY" WO 95/22625; Stemmer and Lipschutz "END COMPLEMENTARY POLYMERASE CHAIN REACTION" WO 96/33207; Stemmer and Crameni "METHODS FOR GENERATING POLYNUCLEOTIDES HAVING DESIRED CHARACTERISTICS BY ITERATIVE SELECTION AND RECOMBINATION" WO 97/0078; Minshul and Stemmer, "METHODS AND COMPOSITIONS FOR CELLULAR AND METABOLIC ENGINEERING" WO 97/35966; Punnonen et al. "TARGETING OF GENETIC VACCINE VECTORS" WO 99/41402; Punnonen et al. "ANTIGEN LIBRARY IMMUNIZATION" WO 99/41383; Punnonen et al. "GENETIC VACCINE VECTOR ENGINEERING" WO 99/41369; Punnonen et al. OPTIMIZATION OF IMMUNOMODULATORY PROPERTIES OF GENETIC VACCINES WO 9941368; Stemmer and Crameri, "DNA MUTAGENESIS BY RANDOM FRAGMENTATION AND REASSEMBLY" EP 0934999; Stemmer "EVOLVING CELLULAR DNA UPTAKE BY RECURSIVE SEQUENCE RECOMBINATION" EP 0932670; Stemmer et al., "MODIFICATION OF VIRUS TROPISM AND HOST RANGE BY VIRAL GENOME SHUFFLING" WO 9923107; Apt et al., "HUMAN PAPILLOMAVIRUS VECTORS" WO 9921979; Del Cardayre et al. "EVOLUTION OF WHOLE CELLS AND ORGANISMS BY RECURSIVE SEQUENCE RECOMBINATION" WO 9831837; Patten and Stemmer, "METHODS AND COMPOSITIONS FOR POLYPEPTIDE ENGINEERING" WO 9827230; Stemmer et al., and "METHODS FOR OPTIMIZATION OF GENE THERAPY BY RECURSIVE SEQUENCE SHUFFLING AND SELECTION" WO9813487.

Certain U.S. Applications provide additional details regarding DNA shuffling and related techniques, as well as other diversity generating methods, including "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, U.S. Ser. No. 09/407,800; "EVOLUTION OF WHOLE CELLS AND ORGANISMS BY RECURSIVE SEQUENCE RECOMBINATION", by del Cardyre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392) and filed Jan. 18, 2000 (PCT/US00/01202) and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393); and "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118854) and filed Oct. 12, 1999 (U.S. Ser. No. 09/416,375) and U.S. Ser. No. 09/484,850 and PCT/US00/01203 filed Jan. 18, 2000.

As review of the foregoing publications, patents, published applications and U.S. patent applications reveals, recursive recombination of nucleic acids to provide new nucleic acids with desired properties can be carried out by a number of established methods and these procedures can be combined with any of a variety of other diversity generating methods.

In brief, at least 5 different general classes of recombination methods are applicable to the present invention and set forth in the references above. First, insertion-modified nucleic acids can be recombined in vitro by any of a variety of techniques discussed in the references above, including e.g., DNAse digestion of nucleic acids to be recombined followed by ligation and/or PCR reassembly of the nucleic acids. Second, insertion modified nucleic acids can be recursively recombined in vivo, e.g., by allowing recombination to occur between nucleic acids in cells. Third, whole genome recombination methods can be used in which whole genomes of cells or other organisms are recombined, optionally including spiking of the genomic recombination mixtures with insertion modified nucleic acids. Fourth synthetic recombination methods can be used, in which oligonucleotides corresponding to targets of interest (e.g., including one or more insertion-modified nucleic acid) are synthesized and reassembled in PCR and/or ligation reactions which include oligonucteotides which correspond to more than one parental nucleic acid (e.g., including, one or more insertion-modified nucleic acid), thereby generating new recombined insertion modified nucleic acids. Oligonucleotides can be made by standard nucleotide addition methods, or can be made, e.g., by tri-nucleotide synthetic approaches. Fifth, in silico methods of recombination can be effected in which genetic algorithms are used in a computer to recombine sequence strings which correspond to nucleic acid homologues (or even non-homologous) insertion modified sequences. The resulting recombined sequence strings are optionally converted into nucleic acids by synthesis of nucleic acids which correspond to the recombined sequences, e.g., in concert with oligonucleotide syrnthesis/gene reassembly techniques. Any of the preceding general recombination formats can be practiced in a reiterative fashion to generate a more diverse set of recombinant nucleic acids.

The above references provide these and other basic recombination formats as well as many modifications of these formats. Regardless of the format which is used, the nucleic acids of the invention can be recombined (with each other or with related (or even unrelated) nucleic acids to produce a diverse set of recombinant nucleic acids, including, e.g., sets of homologous or non-homologous insertion modified nucleic acids.

Following recombination, any nucleic acids which are produced can be selected for a desired activity. In the context of the present invention, this can include testing for and identifying any activity that can be detected, including in an automatable format, by any of the assays in the art. A variety of related (or even unrelated) properties can be assayed for, using any available assay.

DNA shuffling and related techniques provide a robust, widely applicable, means of generating diversity useful for the engineering of proteins, pathways, cells and organisms with improved characteristics. In addition to the basic formats described above, it is sometimes desirable to combine recombination methodologies with other techniques for generating diversity. In conjunction with (or separately from) recombination-based methods, a variety of other diversity generation methods can be practiced and the results (i.e., diverse populations of nucleic acids) screened for. Additional diversity can be introduced into insertion modified nucleic acids by methods which result in the alteration of individual nucleotides or groups of contiguous or non-contiguous nucleotides, e.g., mutagenesis methods. Mutagenesis methods include, for example, recombination (PCT/US98/05223; Publ. No. WO98/42727); oligonucleotide-directed mutagenesis (for review see, Smith, *Ann. Rev. Genet.* 19: 423–462 (1985)); Botstein and Shortle, *Science* 229: 1193–1201 (1985); Carter, *Biochem.* J. 237: 1–7 (1986); Kunkel, "The efficiency of oligonucleotide directed mutagenesis" in *Nucleic acids & Molecular Biology*, Eckstein and Lilley, eds., Springer Verlag, Berlin (1987)). Included among these methods are oligonucleotide-directed mutagenesis (Zoller and Smith, *Nucl. Acids Res.* 10: 6487–6500 (1982), *Methods in Enzymol.* 100: 468–500 (1983), and *Methods in Enzymol.* 154: 329–350 (1987),) phosphothioate-modified DNA mutagenesis (Taylor et al., *Nucl. Acids Res.* 13: 8749–8764 (1985); Taylor et al., *Nucl. Acids Res.* 13: 8765–8787 (1985); Nakamaye and Eckstien, *Nucl. Acids Res.* 14: 9679–9698 (1986); Sayers et al., *Nucl. Acids Res.* 16:791–8012 (1988). Sayers et al., *Nucl. Acids Res.* 16: 803–814 (1988)), mutagenesis using uracil-containing templates (Kunkel, *Proc. Nat'l. Acad. Sci. USA* 82: 488–492 (1985) and Kunkel et al., *Methods in Enzymol.* 154:367–382)); mutagenesis using gapped duplex DNA (Kramer et al., *Nucl. Acids Res.* 12: 9441–9456 (1984); Kramer and Fritz, *Methods in Enzymol.* 154:350–367 (1987); Kramer et al., *Nucl. Acids Res.* 16: 7207 (1988)); and Fritz et al., *Nucl. Acids Res.* 16: 6987–6999 (1988)). Additional suitable methods include point mismatch repair (Kramer et al., *Cell* 38: 879–887 (1984)), mutagenesis using repair-deficient host strains (Carter et al., *Nucl. Acids Res.* 13: 4431–4443 (1985); Carter, *Methods in Enzymol.* 154: 382–403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond.* A 317: 415–423 (1986)), mutagenesis by total gene synthesis (Nambiar et al., *Science* 223: 1299–1301 (1984); Sakamar and Khorana, *Nucl. Acids Res.* 14: 6361–6372 (1988); Wells et al., *Gene* 34:315–323 (1985); and Grundstrom et al., *Nucl. Acids Res.* 13: 3305–3316 (1985). Kits for mutagenesis are commercially available (e.g., Bio-Rad, Amersham International, Anglian Biotechnology).

Other relevant references which describe methods of diversify nucleic acids include Schellenberger U.S. Pat. No. 5,756,316; U.S. Pat. No. 5,965,408; Ostermeier et al. (1999) "A combinatorial approach to hybrid enzymes independent of DNA homology" *Nature Biotech* 17: 1205; U.S. Pat. No. 5,783,43 1; U.S. Pat. No. 5,824,485; U.S. Pat. No. 5,958, 672; Jirholt et al. "Exploiting sequence space: shuffling in vivo formed complementarity determining regions into a master framework" Gene 215: 47 1; U.S. Pat. No. No. 5,939,250; WO 99/10539; WO 98/58085 and WO 99/10539.

Any of these diversity generating methods can be combined, in any combination selected by the user, to produce nucleic acid diversity, which may be screened for using any available screening method.

Example: Selection Strategies for Yeast

Libraries of genes comprising insertion sequences can be recursively shuffled by reccombination and selection to enrich for genes which splice efficiently. For example, a yeast two hybrid system can be used, by, for example, fusing reporter domains to the amine and carboxy terminus of the gene of interest. Stop codons can be incorporated into the introns so that all of the introns have to be removed by splicing to produce a full length protein treat can function in the yeast two hybrid selection. Simply fusing a gene to a selectable reporter such as His3 in yeast allows for positive selection for efficient splicing. Similar approaches can be taken in other eukaryotes, or in bacteria or archaebacteria.

HYBRIDIZATION OF NUCLEIC ACIDS

When there is no explicit knowledge about the ancestry of two nucleic acids, homology is typically inferred by sequence comparison between two sequences. Where two nucleic acid sequences show sequence similarity it is inferred that the two nucleic acids share a common ancestor. The precise level of sequence similarity required to establish homology varies in the art depending on a variety of factors. For purposes of this disclosure, two sequences are considered homologous where they share sufficient sequence identity to allow recombination to occur between two nucleic acid molecules. Typically, nucleic acids require regions of close similarity spaced roughly the same distance apart to permit recombination to occur. Typically, regions of at least about 60% sequence identity or higher are optimal for recombination.

The terms "identical" or percent "identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection. Similarly, the phrase "substantially identical," in the context of to nucleic acids or polypeptides, refers to two or more sequences or subsequence, that have al least about 40%, preferably 80%, most preferably 90–95% nucleotide or amino acid residue identity, when compared and aligned for maximum correspondence, as measured using one of the following sequence comparison algorithms, or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 30 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical/homologous is that the two molecules hybridize to each other under stringent conditions. The phrase "hybridizing specifically to," refers to the binding, duplexing, or hybridizing of a molecule only to a particular nucleotide sequence under stringent conditions, including when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired hybridization of the target polynucleotide sequence. "Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also) be achieved with the addition of destabilizing agents such as formamide. In general, a signal to noise ratio of 2× (or higher) than that observed for an unrelated probe in the particular hybridization assay indicates detection of a specific hybridization. Similarly, if the signal to noise ratio is less than 25% as high as that observed for a perfectly matched probe under stringent conditions, the nucleic acids do not "hybridize under stringent conditions" as that term is used herein. This does not apply to highly stringent conditions, as the stringency can theoretically be increased until only a perfectly matched probe will hybridize.

In one example hybridization procedure, a target nucleic acid to be probed is blotted onto a filter by any conventional method. An unrelated nucleic acid such as a plasimid vector (assuming that the target nucleic acid has no homology with the target nucleic, acid) is also blotted, in approximately equal amounts onto the filter. The filter is probed with a labeled probe complementary to the target nucleic acid. The experiment is repeated at gradually increasing stringency of hybridization and wash conditions until the hybridization of the labeled probe to the complementary target is 10–100× as high as to the unrelated plasmid vector nucleic acid. Once these conditions are determined as described above, a test nucleic acid is probed under the same conditions as the target. If signal from the labeled probe is 25% as high or higher than the signal from binding of the probe to the target, the test nucleic acid "hybridizes under stringent conditions" to the probe. If the signal is less than 25% as high, the test nucleic acid does not hybridize under stringent conditions to the probe.

Post-Recombination Screening Techniques

The precise screening method that is used in the various shuffling procedures herein is not a critical aspect of the invention. In general, one of skill can practice appropriate screening (i.e., selection) methods, by reference to the activity to be selected for.

In any case, one or more recombination cycle(s) is/are optionally followed by at least one cycle of screening or selection for molecules having a desired property or characteristic. If a recombination cycle is performed in vitro, the products of recombination, i.e., recombinant segments, are sometimes introduced into cells before the screening step. Recombinant segments can also be linked to an appropriate vector or other regulatory sequences before screening. Alternatively, products of recombination generated in vitro are sometimes packaged in viruses (e.g., bacteriophage) before screening. If recombination is performed in vivo, recombination products can sometimes be screened in the cells in which recombination occurred. In other applications, recombinant segments are extracted from the cell, and optionally packaged as viruses, before screening.

The nature of screening or selection depends on what property or characteristic is to be acquired or the property or characteristic for which improvement is sought. It is not usually necessary to understand the molecular basis by which particular products of recombination (recombinant segments) have acquired new or improved properties or characteristics relative to the starting substrates. For example, a gene can have many component sequences, each having a different intended role (e.g., coding sequence, regulatory sequences, targeting sequences, stability-conferring sequences, subunit sequences and sequences affecting integration). Each of these component sequences can be varied and recombined simultaneously. Screening/selection can then be performed, for example, for recombinant segments that have increased ability to confer activity upon a cell without the need to attribute such improvement to any of the individual component sequences of the vector.

Depending or the particular screening protocol used for a desired property, initial round(s) of screening can sometimes be performed using bacterial cells due to high transfection efficiencies and ease of culture. However, bacterial expression is often not practice or desired, and yeast, fungal or other eukaryotic systems are also used for library expression and screening. Similarly, other types of screening which are not amenable to screening in bacterial or simple eukaryotic library cells, are performed in cells selected for use in an environment close to that of their intended use. Final rounds of screening can be performed in the precise cell type of intended use.

If further improvement in a property is desired, at least one and usually a collection of recombinant segments (e.g., which include insertion modified sequences) surviving a first round of screening/selection are subject to a further round of recombination. These recombinant segments can be recombined with each other or with exogenous segments representing the original substrates or further variants thereof. Again, recombination can proceed in vitro or in vivo. If the previous screening step identifies desired recombinant segments as components of cells, the components can be subjected to further recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screering/selection can be increased between rounds. Also, the nature of the screen and the property being screened for can vary between rounds if improvement in more than one properly is desired or if acquiring more than one new property is desired. Additional rounds of recombination and screening can then be performed until the recombinant segments have sufficiently evolved to acquire the desired new or improved property or function.

INTEGRATED ASSAYS AND INTEGRATED SYSTEM ELEMENTS

One aspect of the present invention is the alignment of nucleic acids using a computer and sequence alignment software. In addition, other integrated system components provide for high-throughput screening assays, as well as for the coupling of such assays to gene or nucleic acid selection, synthesis and recombination.

Of course, the relevant assay will depend on the application. Many assays for proteins, receptors, ligands and the like are known. Formats include binding to immobilized components, cell or orcanismal viability, production of reporter compositions, and the like.

In the high throughput assays of the invention, it is possible to screen up to several thousand different shuffled variants in a single day. In particular, each well of a microtiter plate can be used to run a separate assay, or, if concentration or incubation time effects are to be observed, every 5–10 wells can test a single variant. Thus, a single standard microtiter plate can assay about 100 (e.g., 96) reactions. If 1536 well plates are used, then a single plate can easily assay from about 100- about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. In addition, "one pot" screening approaches can screen millions of cells or viruses for a desired property, with the cells or viruses being cloned by limiting dilution. Microfluidic approaches to reagent manipulation have also been developed, e.g., by Caliper Technologies (Mountain View, Calif.). Additional details regarding automated shuffling methods are found in Bass et al. "INTEGRATED SYSTEMS AND METHODS FOR DIVERSITY GENERATION AND SCREENING" U.S. Ser. No. 60/175,551, filed Jan. 11, 2000.

In one aspect, library members, e.g., cells, viral plaques, spores or the like, are separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or myelin) and spores (or viruses in plaque applications). The time the pin is in the colony, the number of dies to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells and the dispersal of mycelial fragments similar to the blades of a fermenter. Clones from cultures of interest can be cloned by limiting dilution. As also described supra, plaques or cells constituting libraries can also be screened directly for production of proteins, either by detecting hybridization, protein activity, protein binding to antibodies, or the like.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the present invention, e.g., for high-throughput screening of molecules assembled from the various oligonucleotide sets described herein. The nature and implementation of modifications to these devices (if any) so that they can operate as discussed herein with, reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Optical images viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip- compatible DOS™, OS2™ WINDOWS™, WINDOWS NT™ or WINDOWS95™ based machines), MACINTOSH™, or UNIX based (e.g., SUN™ work station) computers. One conventional system carries light from the assay device to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Integrated systems for assay analysis in the present invention typically include a digital computer with high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled assay components. The image scanner interfaces with the image analysis software to provide a measurement of probe label intensity.

Of course, these assay systems can also include integrated systems incorporating nucleic acid selection elements, such as a computer, database with nucleic acid sequences of interest sequence alignment software, and oligonucleotide selection software. In addition, this software can include components for ordering the selected oligonucleotides, and/or directing synthesis of oligonucleotides by an operably linked oligonucleotide synthesis machine. Thus, the integrated system elements of the invention optionally include any of the above components to facilitate high throughput recombination and selection. It will be appreciated that these high-throughput recombination elements can be in systems separate from those for performing selection assays, or the two can be integrated.

EXAMPLE: SHUFFLING OF A CYTOKINE

Libraries of synthetic genes of a cytokine (designated Cytokine G) were generated that contain 3 introns at positions which are new as compared to any known natural form of the cytokine. The introns were derived from several human globin genes. In addition, splice site quasispecies were included to provide for multiple splice site sequences. The intron containing genes were cloned into a vector that allowed expression of the encoded proteins on the surface of transfected cells. The vector also encodes a C-terminal epitope tag that allows the detection of expressed proteins by FACS or Western blot using an epitope-specific antibody.

The constructs were transfected into COS cells using protoplast fusion or superfect transfection. Upon splicing of the inserted introns in the transfected cells, translation of the spliced mRNA generated proteins presented on the cell surface that contained the epitope tag. Using FACS, expression of protein containing the epitope tag was detected in the libraries. Cells expressing protein were isolated by FACS sorting, and the transfected library inserts were isolated by PCR and recloned into the same expression vector. Upon retransfection of the PCR-rescued constructs, an enrichment of cells expressing epitope-tagged protein was observed. These observations suggest that library species which support splicing of the inserted introns were selected for.

Modifications can be made to the method and materials as hereinbefore described without departing from the spirit or scope of the invention as claimed, and the invention can be put to a number of different uses, including:

The use of an integrated system to select and test insertion modified and/or shuffled nucleic acids for activity, including in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a recombination or insertion component as described herein; (2) instructions for practicing the methods described herein, and/or for operating oligonucleotide synthesis or assembled gene selection procedures herein; (3) one or more assay component; (4) a container for holding nucleic acids, intron nucleic acids, intein sequences, enzymes, other nucleic acids, transgenic plants, animals, cells, or the like and, (5) packaging materials.

In a further aspect, the present invention provides for the use of any component or kit herein, for the practice of any method or assay herein, and/or for the use of any apparatus or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques and materials described above can be used in various combinations. All publications and patent documents cited in this application are incorporated by reference in their entirety for all purposes to the same extent as if each individual publication or patent document were so individually denoted.

What is claimed is:

1. A method of recombining a first and a second target DNA, the method comprising:
provproviding a first and a second target DNA, wherein at least one of the first and second target DNAs comprises a plurality of homologous or non-homologous insertion DNA sequences, wherein the plurality of insertion DNA sequences encode one or more intein; and,
recombining the first and second target DNAs, thereby providing a recombinant DNA.

2. The method of claim 1, wherein the method occurs in vitro.

3. The method of claim 2, wherein the recombinant DNA encodes a protein subsequence, which protein subsequence is spliced to a second protein subsequence to produce an active protein.

4. The method of claim 3, wherein the protein subsequence and the second protein subsequence are spliced in vivo.

5. The method of claim 3, wherein the protein subsequence and the second protein subsequence are spliced in cis.

6. The method of claim 3, wherein the protein subsequence and the second protein subsequence are spliced in trans.

7. The method of claim 3, wherein the protein subsequence and the second protein subsequence are spliced in a spontaneous splicing reaction.

8. The method of claim 3, wherein the protein subsequence and the second protein subsequence are spliced in a controlled splicing reaction.

9. The method of claim 1, wherein the plurality of insertion DNA sequences are present in both the first and second target DNAs.

10. The method of claim 1, wherein the plurality of insertion DNA sequences at least partially comprise at least one DNA subsequence which encodes at least one trans-splicing intein.

11. The method of claim 1, wherein the first or second target DNA comprises at least about 10 mini exteins.

12. The method of claim 1, wherein the first or second target DNA comprises at least about 10 insertion DNA sequences.

13. The method of claim 1, wherein the insertion DNA sequences modulate a recombination frequency between the first and second target DNAs.

14. The method of claim 1, wherein the insertion DNA sequences modulate an expression level or expression pattern of the first target DNA, the second target DNA, or the recombinant DNA in one or more cells.

15. The method of claim 1, wherein the insertion DNA sequences are recombined with one or more parental DNAs to produce the first or second target DNA.

16. The method of claim 1, the method further comprising:
providing a first parental DNA sequence and a second parental DNA sequence, which first and second parental DNA sequences are homologous or non-homologous; and,
inserting a plurality of insertion DNA sequences into one or more of the first and second parental DNA sequences, wherein the plurality of insertion DNA sequences encode one or more intein, thereby providing the first and the second target DNAs.

17. The method of claim 16, wherein the step of inserting the plurality of insertion DNA sequences into one or more of the first and second parental DNA sequences is performed by physically joining a plurality of subsequences of the first or second parental DNA sequences to the plurality of insertion DNA sequences.

18. The method of claim 1, the method further comprising selecting the recombinant DNA for a desired trait or property.

19. The method of claim 1, further comprising expressing the recombinant DNA in a cell.

20. The method of claim 1, further comprising expressing the recombinant DNA in a cell, thereby producing a protein, which protein is proteolytically cleaved to produce an active protein or to remove the intein.

21. The method of claim 1, the first and second target DNAs each comprising a plurality of insertion DNAs, wherein, during recombination of the first and second target DNAs, the crossover frequency between the insertion sequences in the first and second DNAs is higher than the crossover frequency of non-insertion sequences in the first and second target DNAs.

22. The method of claim 1, wherein the recombinant DNA encodes a molecule which does not comprise or encode a translated insertion sequence.

23. The method of claim 22, wherein the molecule is selected from a DNA, an RNA, an mRNA, a viral RN,A a sn RNA, a tRNA, an rRNA, a gRNA, a protein, and a proteolytically cleaved protein.

24. The method of claim 1, wherein the recombinant DNA encodes a protein with an activity selected from an insulin protein activity, a peptide hormone activity, a cytokine activity, an epidermal growth factor activity, a fibroblast growth factor activity, a hepatocyte growth factor activity, an insulin-like growth factor activity, an interferon activity, an interleukin activity, a keratinocyte growth factor activity, a leukemia inhibitory factor activity, an oncostatin M activity, a PD-ECSF activity, a pleiotropin activity, an SCF activity, a c-kit ligand activity, a VEGF activity, a G-CSF activity, an oncogene activity, a tumor suppressor activity, a steroid hormone receptor activity, an herbicide resistance activity, a monooxygenase activity, a nuclease activity, a lipase activity, an antibody V gene activity, a TGFβ activity, an NGF activity, a PDGFβ activity, a TNK$_{or}$ activity, a CNTF activity, a 4F activity, an RNase activity, an antibody activity, a tumor necrosis factor activity, a GM-CSF activity, a plant hormone activity, a disease resistance protein activity, a bacterial protein activity, a protease activity, a peptide ligand activity, a angiogenisis inhibitor activity, a C-X-C chemokine activity, a C—C chemokine activity, a cystein knot protein activity, and an EPO activity, wherein the recombinant nucleic acid does not hybridize under stringent conditions to a cDNA which encodes said activity, which cDNA is a copy of a naturally occurring mRNA.

25. The method of claim 1, wherein the first target DNA comprises two non-homologous subsequences and a plurality of insertion subsequences.

26. The method of claim 1, wherein the first or second target DNA or recombinant DNA is present in an expression vector.

27. A method of recombining a first and a second target nucleic acid, the method comprising:
providing a first and a second target nucleic acid, wherein at least one of the first and second target nucleic acids comprises a plurality of homologous or non-homologous insertion nucleic acid sequences, wherein the insertion nucleic acid sequences comprise at least one intein; and,
recombining the first and second target nucleic acids, thereby providing a recombinant nucleic acid,
wherein the recombinant nucleic acid encodes a protein subsequence, and, wherein the protein subsequence and the second protein subsequence are spliced in vitro to produce an active protein.

28. A method of recombining a first and a second target nucleic acid, the method comprising:
providing one or more parental nucleic acids, wherein at least one of the parental nucleic acids is recombined with a plurality of insertion nucleic acid sequences, thereby providing a first or a second target nucleic acid, wherein at least one of the first and second target nucleic acids comprises the plurality of homologous or non-homologous insertion nucleic acid sequences; and,
recombining the first and second target nucleic acids, thereby providing a recombinant nucleic acid,
wherein the parental nucleic acid corresponds to one or more of: a gene or cDNA encoding EPO, a gene or cDNA encoding an insulin protein, a gene or cDNA encoding a peptide hormone, a gene or cDNA encoding a cytokine, a gene or cDNA encoding an epidermal growth factor, a gene or cDNA encoding a fibroblast growth factor, a gene or cDNA encoding a hepatocyte growth factor, a gene or cDNA encoding insulin-like growth factor, a gene or cDNA encoding an interferon, a gene or cDNA encoding an interleukin, a gene or cDNA encoding a keratinocyte growth factor, a gene or cDNA encoding a leukemia inhibitory factor, a gene or cDNA encoding oncos- tatin M, a gene or cDNA encoding PD-ECSF, a gene or cDNA encoding PDGF, a gene or cDNA encoding pleiotropin, a gene or cDNA encoding SCF, a gene or cDNA encoding c-kit ligand, a gene or cDNA encoding VEGF, a gene or cDNA encoding G-CSF, a gene or cDNA encoding an oncogene, a gene or cDNA encoding a tumor suppressor, a gene or cDNA encoding a steroid hormone receptor, a gene or cDNA encoding a plant hormone, a gene or cDNA encoding a disease resistance gene, a gene or cDNA encoding an herbicide resistance gene, a gene or cDNA encoding a bacterial gene, a gene or cDNA encoding a monooxygenase, a gene or cDNA encoding a protease, a gene or cDNA encoding a nuclease, a gene or cDNA encoding a lipase, a gene or cDNA encoding a C-X-C chemokine, a gene or cDNA encoding a C—C chemokine, a gene or cDNA encoding an antibody V gene, a gene or cDNA encoding a cystein knot protein, a gene or cDNA encoding TGFβ, a gene or cDNA encoding NGF, a gene or cDNA encoding PDGFβ a gene or cDNA encoding a TNKor family member, a gene or cDNA encoding CNTF, a gene or cDNA encoding 4F, a gene or cDNA encoding an RNase, a gene or cDNA encoding an antibody, a gene or cDNA encoding peptide ligand, a gene or cDNA encoding a tumor necrosis factor and a gene or cDNA encoding an angiogenisis inhibitor.

29. The method of recombining a first and a second target nucleic acid, the method comprising:
providing a first parental nucleic acid sequence and a second parental nucleic acid sequence, wherein the first and second parental nucleic acid sequences are homologous or non-homologous;
inserting a plurality of insertion nucleic acid sequences into one or more of the first and second parental nucleic acid sequences, thereby providing first and second target nucleic acids, wherein the first and second parental nucleic acid sequences hybridize under stringent conditions, and the first and second target nucleic acids do not hybridize under stringent conditions; and,
recombining the first and second target nucleic acids, wherein at least one of the first and second target nucleic acids comprises the plurality of homologous or non-homologous insertion nucleic acid sequences, thereby providing a recombinant nucleic acid.

30. The method of recombining a first and a second target nucleic acid, the method comprising:
providing a first parental nucleic acid sequence and a second parental nucleic acid sequence, wherein the first and second parental nucleic acid sequences are homologous or non-homologous;
inserting a plurality of insertion nucleic acid sequences into one or more of the first and second parental nucleic acid sequences, thereby providing the first and the second target nucleic acids, wherein the first and second parental nucleic acid sequences do not hybridize under stringent conditions, and wherein the first and second target nucleic acids hybridize under stringent conditions; and,
recombining the first and second target nucleic acids, wherein at least one of the first and second target nucleic acids comprises the plurality of homologous or non-homologous insertion nucleic acid sequences, thereby providing a recombinant nucleic acid.

31. The method of recombining a first and a second target nucleic acid, the method comprising:

providing a first parental nucleic acid sequence and a second parental nucleic acid sequence, wherein the first and second parental nucleic acid sequences are homologous or non-homologous;

inserting a plurality of insertion nucleic acid sequences into one or more of the first and second parental nucleic acid sequences, thereby providing the first and the second target nucleic acids, wherein the first and second target nucleic acids hybridize under stringent conditions, and wherein the first target nucleic acid does not hybridize under stringent conditions to the second parental nucleic acid, or wherein the second target nucleic acid does not hybridize under stringent conditions to the first parental nucleic acid sequence; and, recombining the first and second target nucleic acids, wherein at least one of the first and second target nucleic acids comprises the plurality of homologous or non-homologous insertion nucleic acid sequences, thereby providing a recombinant nucleic acid.

32. The method of recombining a first and a second target nucleic acid, the method comprising:

providing a first parental nucleic acid sequence and a second parental nucleic acid sequence, wherein the first and second parental nucleic acid sequences are homologous or non-homologous;

inserting a plurality of insertion nucleic acid sequences into one or more of the first and second parental nucleic acid sequences, thereby providing the first and the second target nucleic acids, wherein the first or second parental nucleic acid sequence hybridizes to a third nucleic acid under stringent conditions, wherein the first and second target nucleic acids do not hybridize under stringent conditions to the third nucleic acid; and, recombining the first and second target nucleic acids, wherein at least one of the first and second target nucleic acids comprises the plurality of homologous or non-homologous insertion nucleic acid sequences, thereby providing a recombinant nucleic acid.

33. The method of recombining a first and a second target nucleic acid, the method comprising:

providing a first and a second target nucleic acid, wherein at least one of the first and second target nucleic acids comprises a plurality of homologous or non-homologous insertion nucleic acid sequences;

recombining the first and second target nucleic acids, thereby providing a recombinant nucleic acid; and, recombining the recombinant nucleic acid with a third nucleic acid, and, optionally, selecting the resulting secondary recombinant nucleic acid for a desired trait or property.

34. The method of recombining a first and a second target nucleic acid, the method comprising: providing a first and a second target nucleic acid, wherein at least one of the first and second target nucleic acid comprises a plurality of homologous or non-homologous insertion nucleic acid sequences, wherein the first and second target nucleic acids are derived from first and second parental nucleic acids by integration of a plurality of insertion sequences into the first and second parental nucleic acids, wherein the first and second parental nucleic acid are less than 50% identical over the full length of the first and second parental nucleic acids, when the first and second nucleic acids are aligned for maximum identity; and, recombining the first and second target nucleic acids, thereby providing a recombinant nucleic acid.

35. The method of claim 34, wherein the first and second parental nucleic acids are less than 25% identical over the full length of the first and second parental nucleic acids, when the first and second target nucleic are aligned for maximum identity.

* * * * *